US012594273B2

(12) United States Patent
Haruta et al.

(10) Patent No.: US 12,594,273 B2
(45) Date of Patent: Apr. 7, 2026

(54) INTRANASAL DHE FOR THE TREATMENT OF HEADACHE

(71) Applicant: Satsuma Pharmaceuticals, Inc., Durham, NC (US)

(72) Inventors: Shunji Haruta, Kagoshima-ken (JP); Nikhilesh N. Singh, Mill Valley, CA (US); John Kollins, San Francisco, CA (US); Salvador Rico, Berkeley, CA (US)

(73) Assignee: Satsuma Pharmaceuticals, Inc.

( * ) Notice: Subject to any disclaimer, the term of this patent is extended or adjusted under 35 U.S.C. 154(b) by 0 days.

(21) Appl. No.: 17/834,583

(22) Filed: Jun. 7, 2022

(65) Prior Publication Data

US 2023/0000860 A1 Jan. 5, 2023

Related U.S. Application Data

(63) Continuation of application No. 16/414,350, filed on May 16, 2019, now abandoned, which is a continuation of application No. 15/023,206, filed as application No. PCT/IB2014/002706 on Sep. 24, 2014.

(60) Provisional application No. 61/881,947, filed on Sep. 24, 2013.

(51) Int. Cl.

| | |
|---|---|
| ***A61K 31/4985*** | (2006.01) |
| ***A61K 9/00*** | (2006.01) |
| ***A61K 9/14*** | (2006.01) |
| ***A61K 31/48*** | (2006.01) |
| ***A61K 31/522*** | (2006.01) |
| ***A61K 45/06*** | (2006.01) |
| ***A61K 47/02*** | (2006.01) |
| ***A61K 47/22*** | (2006.01) |
| ***A61K 47/38*** | (2006.01) |
| ***A61P 25/06*** | (2006.01) |

(52) U.S. Cl.

CPC ........ *A61K 31/4985* (2013.01); *A61K 9/0043* (2013.01); *A61K 9/146* (2013.01); *A61K 31/48* (2013.01); *A61K 31/522* (2013.01); *A61K 45/06* (2013.01); *A61K 47/02* (2013.01); *A61K 47/22* (2013.01); *A61K 47/38* (2013.01)

(58) Field of Classification Search

CPC .. A61K 31/4985; A61K 9/0043; A61K 31/48; A61K 47/02; A61K 47/38; A61K 31/522; A61K 2300/00; A61P 25/06

See application file for complete search history.

(56) References Cited

U.S. PATENT DOCUMENTS

| | | | |
|---|---|---|---|
| 4,613,500 | A | 9/1986 | Suzuki et al. |
| 5,169,849 | A | 12/1992 | Kiechel et al. |
| 5,756,483 | A | 5/1998 | Merkus |
| 6,906,027 | B2 | 6/2005 | Oki et al. |
| 7,022,311 | B1 | 4/2006 | Ohkuma et al. |
| 7,638,138 | B2 | 12/2009 | Oki et al. |
| 8,062,670 | B2 | 11/2011 | Baran, Jr. et al. |
| 8,062,970 | B2 | 11/2011 | Tanaka |
| 8,435,554 | B2 | 5/2013 | Oki et al. |
| 8,673,360 | B2 | 3/2014 | Nagata et al. |
| 8,710,092 | B2 | 4/2014 | Zhang et al. |
| 8,827,946 | B2 | 9/2014 | Tsutsui et al. |
| 9,101,539 | B2 | 8/2015 | Nagata et al. |
| 9,138,410 | B2 | 9/2015 | Oki et al. |
| 9,707,226 | B2 | 7/2017 | Keegan et al. |
| 10,195,139 | B2 | 2/2019 | Nagata et al. |
| 10,758,532 | B2 | 9/2020 | Kollins et al. |
| 10,792,253 | B2 | 10/2020 | Haruta |
| 2003/0044458 | A1 | 3/2003 | Wright, IV et al. |
| 2005/0118272 | A1 | 6/2005 | Besse et al. |
| 2005/0158250 | A1 | 7/2005 | Oki et al. |
| 2006/0057213 | A1 | 3/2006 | Larhrib et al. |
| 2006/0147388 | A1 | 7/2006 | Merkus et al. |
| 2007/0253913 | A1 | 11/2007 | Mohsen et al. |
| 2008/0260848 | A1 | 10/2008 | Nagata et al. |
| 2008/0287451 | A1* | 11/2008 | Cook ...................... A61P 25/06 514/250 |
| 2009/0163604 | A1 | 6/2009 | Kakizawa et al. |
| 2009/0217928 | A1 | 9/2009 | Patton et al. |
| 2010/0178331 | A1 | 7/2010 | Nagata et al. |
| 2011/0045088 | A1 | 2/2011 | Tsutsui et al. |
| 2011/0082150 | A1 | 4/2011 | Cook et al. |

(Continued)

FOREIGN PATENT DOCUMENTS

| | | | |
|---|---|---|---|
| CN | 101677954 | A | 3/2010 |
| GB | 1592563 | A | 7/1981 |

(Continued)

OTHER PUBLICATIONS

U.S. Appl. No. 16/933,560 Office Action dated Nov. 29, 2022.

Anjilvel, et al. A multiple-path model of particle deposition in the rat lung. Fundamental and Applied Toxicology 28.1 (1995): 41-50.

Aurora SK, "OnabotulinumtoxinA for treatment of chronic migraine: pooled analyses of the 56-week PREEMPT clinical program", Headache. Oct. 2011;51(9):1358-73. doi: 10.1111/j.1526-4610.2011.01990.x. Epub Aug. 29, 2011.

Berge, et al. Pharmaceutical salts. J Pharm Sci. Jan. 1977;66(1):1-19.

CeolusTM basic information (Asahi Kasei's web site for pharmaceutical excipients), Obtained online on Sep. 17, 2015.

(Continued)

*Primary Examiner* — Mina Haghighatian

(74) *Attorney, Agent, or Firm* — Wilson Sonsini Goodrich & Rosati

(57) ABSTRACT

Presented herein are powder formulations comprising dihydroergotamine (DHE), or a pharmaceutically acceptable salt thereof. In addition to such formulations, also presented herein are methods comprising intranasally administering powder formulations comprising dihydroergotamine, or a pharmaceutically acceptable salt thereof. The presented methods can be used for treating headache, for example, for rapid onset treatment of headache, including migraine, e.g. acute treatment of migraine with or without aura.

16 Claims, 6 Drawing Sheets

(56) References Cited

U.S. PATENT DOCUMENTS

Figure 1:
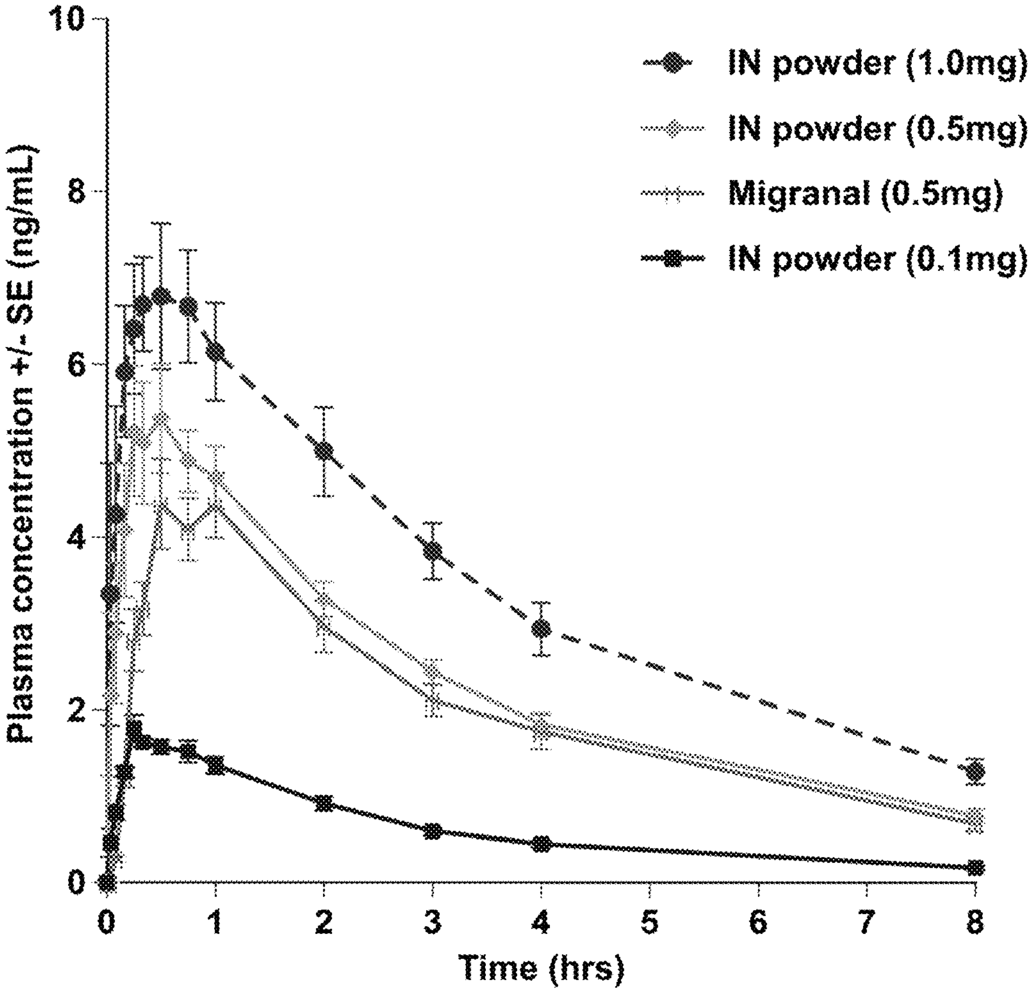

| | | | |
|---|---|---|---|
| 2011/0171141 A1 | 7/2011 | Kellerman et al. | |
| 2011/0318277 A1* | 12/2011 | Dalby | A61P 37/06 424/45 |
| 2013/0095145 A1 | 4/2013 | Nagata et al. | |
| 2013/0129781 A1 | 5/2013 | Nagata et al. | |
| 2013/0178465 A1* | 7/2013 | Henwood | A61P 25/00 604/207 |
| 2014/0014104 A1 | 1/2014 | Hoekman et al. | |
| 2014/0179704 A1 | 6/2014 | Kellerman et al. | |
| 2014/0179705 A1 | 6/2014 | Armer et al. | |
| 2015/0238412 A1 | 8/2015 | Kellerman et al. | |
| 2016/0228433 A1 | 8/2016 | Haruta et al. | |
| 2018/0036247 A1 | 2/2018 | Haruta | |
| 2019/0000753 A1 | 1/2019 | Narasimha Murthy et al. | |
| 2019/0091424 A1 | 3/2019 | Haruta | |
| 2019/0209463 A1 | 7/2019 | Hoekman et al. | |
| 2019/0275036 A1 | 9/2019 | Haruta et al. | |
| 2020/0179379 A1 | 6/2020 | Haruta et al. | |
| 2020/0345730 A1 | 11/2020 | Kollins et al. | |
| 2024/0108619 A1 | 4/2024 | Haruta et al. | |

FOREIGN PATENT DOCUMENTS

| | | |
|---|---|---|
| JP | H1059841 A | 3/1998 |
| JP | 2003206227 A | 7/2003 |
| JP | 2005520799 A | 7/2005 |
| JP | 2006519219 A | 8/2006 |
| JP | 4721212 B2 | 7/2011 |
| JP | 2013126989 A | 6/2013 |
| JP | 2018076305 A | 5/2018 |
| WO | WO-9422445 A2 | 10/1994 |
| WO | WO-0027373 A1 | 5/2000 |
| WO | WO-2004073729 A1 | 9/2004 |
| WO | WO-2006016530 A1 | 2/2006 |
| WO | WO-2008097664 A1 | 8/2008 |
| WO | WO-2012105236 A1 | 8/2012 |
| WO | WO-2012119153 A2 | 9/2012 |
| WO | WO-2015044782 A2 | 4/2015 |
| WO | WO-2018025089 A2 | 2/2018 |
| WO | WO-2019065673 A1 | 4/2019 |
| WO | WO-2019136291 A1 | 7/2019 |
| WO | WO-2020123607 A1 | 6/2020 |

OTHER PUBLICATIONS

Detlef Albrecht et al., Pharmacokinetics and Safety of Intranasal Dihydroergotamine Powder (STS101), American Headache Society 61st Annual Scientific Meeting, Jul. 11-14, 2019, Philadelphia, PA.
Edwards KR et al., "Comparison of intravenous valproate versus intramuscular dihydroergotamine and metoclopramide for acute treatment of migraine headache", Headache. Nov.-Dec. 2001;41(10):976-80.
Elbrond et al, Pharmacokinetics, Pharmacodynamics, Safety, and Tolerability of a Single-Dose of N N2211, a Long-Acting Glucagon Like Peptide 1 Derivative, in Healthy Male Subjects, Diabetes care, vol. 25, No. 8, Aug. 2002.
EP21205407.6 Extended Search Report dated May 11, 2022.
European search report and opinion dated Aug. 17, 2022 for EP Application No. 19894836.6.
Fasiolo, Laura Tiozzo et al., "Opportunity and challenges of nasal powders:Drug formulation and delivery", European Journal of Pharmaceutical Sciences, 2017, 1-16.
Fumiyoshi Iwashima et al., "STS101 (Dry Powder Intranasal Dihydroergotamine) Drug-Device Combination Achieves Consistent and Robust Delivery Performance for Migraine Patients", presented at the International headache Conference, Sep. 5-8, 2019.
Gallagher, R. Michael, "Acute Treatment of Migraine With Dihydroergotamine Nasal Spray", Arch Neurol 1996;53:1285-1291.
Gavezzotti. Are crystal structures predictable? Accounts of chemical research 27.10 (1994): 309-314.
Humbert H et al., "Human pharmacokinetics of dihydroergotamine administered by nasal spray", Clin Pharmacol Ther. Sep. 1996;60(3):265-75.
Ilium, Nasal drug delivery: New developments and strategies, research focus, DDT vol. 7, No. 23, Dec. 2002.
International search report and written opinion dated Mar. 20, 2015 for PCT/IB2014/002706.
International Search Report and Written Opinion dated Apr. 8, 2020 for International Application Serial No. PCT/US2019/065647, (8 pages).
J. N. J. M. de Hoon et al., "Dihydroergotamine: discrepancy between arterial, arteriolar and pharmacokinetic data", J. Clin Pharmacol, 2001, 52, 45-51.
Jaipal, A. et al., Effect of HPMC and mannitol on drug release and bioadhesion behavior of buccal discs of buspirone hydrochloride: In-vitro and in-vivo pharmacokinetic studies, Saudi Pharmaceutical Journal (2015) 23, 315-326.
Kellerman, Donald J. et al., "Assessment of the Consistency of Absorption of Dihydroergotamine Following Oral Inhalation: Pooled Results from Four Clinical Studies", Journal of Aerosol and Pulmonary Drug Delivery, 2013, vol. 26, No. 5, pp. 297-306.
Kelsey Satterly et al., "Comparison of Early Plasma Exposure of DHE Following Delivery by Nasal, Oral Inhalation or Intravenous Administration", presented at the 2019 American Headache Society Annual Meeting Jul. 11-14, 2019, Philadelphia, PA.
Le. Merck Manuals Professional Edition. Overview of Pharmacokinetics. Obtained online Sep. 2020.
Marttin, Emmeline et al. "Nasal Absorption of Dihydroergotamine from Liquid and Powder Formulations in Rabbits", Journal of Pharmaceutical Sciences, 1997, vol. 86, No. 7, 802-807.
Marttin, et al. Nasal absorption of dihydroergotamine from liquid and powder formulations in rabbits. J Pharm Sci. Jul. 1997;86(7):802-7.
Migranal® US Food and Drug Administration, Summary Basis of Approval, 1997.
Notice of Allowance dated Jul. 17, 2020 for U.S. Appl. No. 16/710,538.
Noveck, Robert J et al. "Assessing acute systemic effects of an inhaled drug with serial echocardiography: a placebo-controlled comparison of inhaled and intravenous dihydroergotamine." Drug design, development and therapy vol. 7 619-25. Jul. 24, 2013, doi:10.2147/DDDT.S44093.
Office action dated Apr. 23, 2020 for U.S. Appl. No. 16/710,538.
Office action dated Apr. 27, 2022 for U.S. Appl. No. 16/933,560.
Office Action dated Sep. 27, 2017 for U.S. Appl. No. 15/023,206.
Office action dated Sep. 29, 2021 for U.S. Appl. No. 16/933,560.
Office action dated Jan. 30, 2017 for U.S. Appl. No. 15/023,206.
Olorunsola, Emmanuel O. et al., Evaluation of Chitosan-Microcrystalline Cellulose Blends as Direct Compression Excipients, Hindawi, Journal of Drug Delivery (2017) Article ID 8563858, 8 pages, https:ildoi.orgi10.1155/2017/8563858.
Price, et al. Multiple Path Particle Dosimetry model (MPPD v1.0): A model for human and rat airway particle dosimetry. RIVM Report 650010030. Published Dec. 11, 2002.
Robert O. Cook, PhD et al., "Reduced Adverse Event Profile of Orally Inhaled DHE (MAP0004) vs IV DHE: Potential Mechanism", Headache, 2009:49, 1423-1434.
S. Mellander and I. Nordenfelt, "Comparative Effects of Dihydroergotamine and Noradrenaline on Resistance Exchange and Capacitance Functions in the Peripheral Circulation", Clinical Science, 1970, 39, 183-201.
Schran, Horst F. et al., "Bioequivalence and Safety of Subcutaneously and Intramuscularly Administered Dihydroergotamine in Healthy Volunteers", Current Therapeutic Research, Dec. 1994; vol. 55, No. 12, 8 pages.
Shah et al. The role of fluorine in medicinal chemistry. Journal of Enzyme Inhibition and Medicinal Chemistry 22(5):527-540 (Oct. 2007).
Shannon Strom, PhD et al., "Comparison of the Pharmacokinetics of STS101, an Intranasal Dry Powder Formulation of Dihydroergotamine, with Other Intranasal, Injectable, and Oral Inhaled DHE Formulations", IHC-PO-362, presented at the International Headache Conference, Sep. 5-8, 2019.

(56) References Cited

OTHER PUBLICATIONS

Shrewsbury SB et al., “Safety, Tolerability and Comparative Bioavailability of a Novel Intranasal DHE Product (INP104)”, Headache, presented at the American Headache Society 60th Annual Meeting, Jun. 28-Jul. 1, 2018, San Francisco, CA.
Shrewsbury SB et al., “STOP 301: Open-label Safety and Tolerability of Chronic Intermittent Usage for 24/52 Weeks of INP104 [Nasal Dihydroergotamine Mesylate (DHE) Administered by Precision Olfactory Delivery (POD) Device] in Migraine Headach)”, Headache, presented at the 2019 American Headache Society Annual Meeting, Jul. 11-14, 2019, Philadelphia, PA.
Sieneke Labruijere et al., “Dihydroergotamine and sumatriptan in isolated human coronary artery, middle meningeal artery and saphenous”, Cephalalgia, 2015, vol. 35(2), 182-189.
Silberstein SD et al., “Efficacy and safety of topiramate for the treatment of chronic migraine: a randomized, double-blind, placebo-controlled trial”, Headache. Feb. 2007;47(2):170-80.
Stephen B. Shrewsbury, MB ChB, FFPM, MAHA et al., “STOP 101: A Phase 1, Randomized, Open-Label, Comparative Bioavailability Study of INP104, Dihydroergotamine Mesylate (DHE) Administered Intranasally by a 1123 Precision Olfactory Delivery (POD) Device, In Healthy Adult Subjects”, Headache, 2019, 1-16.
Stephen D. Silberstein, MD et al., “Dihydroergotamine (DHE)—Then and Now: A Narrative Review”, Headache, 2019, 1-18.
U.S. Appl. No. 15/023,206 Final Office Action date Feb. 12, 2020.
U.S. Appl. No. 15/023,206 Office Action dated Apr. 24, 2018.
U.S. Appl. No. 15/023,206 Office Action dated Dec. 19, 2018.
U.S. Appl. No. 15/023,206 Office Action dated Jan. 30, 2017.
U.S. Appl. No. 15/023,206 Office Action dated Oct. 1, 2020.
U.S. Appl. No. 16/414,350 Office Action date Apr. 19, 2021.
U.S. Appl. No. 16/414,350 Office Action date Aug. 31, 2020.
U.S. Appl. No. 16/414,350 Office Action dated Dec. 7, 2021.
U.S. Appl. No. 16/791,431 Non-Final Office Action dated Mar. 2, 2021.
U.S. Appl. No. 16/791,431 Office Action date Aug. 27, 2020.
U.S. Appl. No. 16/791,431 Office Action dated Jun. 15, 2020.
U.S. Appl. No. 15/023,206 Non-Final Office Action date Aug. 27, 2019.
U.S. Appl. No. 16/414,350 Final Office Action dated Dec. 2, 2019.
U.S. Appl. No. 16/414,350 Non-Final Office Action dated Jul. 10, 2019.
Van Der Kuy, et al. Bioavailability of intranasal formulations of dihydroergotamine. Eur J Clin Pharmacol. Nov. 1999;55(9):677-680. doi: 10.1007/s002280050692.
Van Gerven, et al. Enhanced chemosensory sensitivity in patients with idiopathic rhinitis and its reversal by nasal capsaicin treatment. J Allergy Clin Immunol. Aug. 2017;140(2):437-446.e2. doi: 10.1016/j.jaci.2017.03.014. Epub Apr. 4, 2017.
Vehovec, Tanja et al., Influence of different types of commercially available microcrystalline cellulose on degradation of perindopril erbumine and enalapril maleate in binary mixtures, Acta Pharm. 62 (2012) 515-528, DOI: 10.2478/v10007-012-0039-5.
W. H. Aellig, “Investigation of the Venoconstrictor Effect of 8' Hydroxydihydroergotamine, the Main Metabolite of Dihydroergotamine, in Man”, European Journal of Clinical Pharmacology, 1984, 26:239-242.
Whyte, MD, Chad A., “Dihydroergotamine and its Use in Migraine With Posterior Fossa Symptoms”, Headache, 2010:50, 1419-1423.
Wurm, M. et al., “Comparative Trial of the Peripheral Vascular Effects of Dihydroergotamine Administered via the Intranasal and Intramuscular Routes”, Institut de Recherches Cardiovasculaires ROYAT, Sandoz Laboratories, Pharmaceutical Research Center, 426-427.Undated.
International Headache Society Committee on Clinical Trials in Migraine. Cephalalgia. vol. 11, 1991. pp. 1-12.
Migranal® Nasal Spray (dihydroergotamine mesylate, USP)—Package Insert N 20-148/ S-007 S-008. E-signed by R. Katz on Jul. 31, 2002. 23 pages.
Novartis. D.H.E. 45 (dihydroergotamine mesylate) Injection, USP—Prescribing Information; Package Insert. Signed by R. Katz Jul. 31, 2002. 37 pages.
U.S. Appl. No. 16/933,560 Office Action dated Jun. 16, 2023.
Co-pending U.S. Appl. No. 18/479,335, inventors Haruta; Shunji et al., filed on Oct. 2, 2023.
U.S. Appl. No. 16/933,560 Office Action dated Nov. 22, 2023.
U.S. Appl. No. 15/023,206 Office Action dated Aug. 27, 2019.
U.S. Appl. No. 16/791,431 Office Action dated Apr. 13, 2020.
U.S. Appl. No. 18/479,335 Office Action dated Jan. 24, 2024.

* cited by examiner

INTRANASAL DHE FOR THE TREATMENT OF HEADACHE

1. CROSS-REFERENCE

This application is a continuation of U.S. patent application Ser. No. 16/414,350 filed May 16, 2019, which is a continuation of U.S. patent application Ser. No. 15/023,206 filed Mar. 18, 2016, which is National Stage Entry of PCT/IB2014/002706 filed Sep. 24, 2014, which claims the benefit of U.S. Provisional Patent Application Ser. No. 61/881,947, filed Sep. 24, 2013, each of which is entirely incorporated herein by reference.

2. BACKGROUND

Migraine is a very common, often debilitating, form of headache. Typically the headache is unilateral (affecting one half of the head) and pulsating in nature. In addition to head pain, associated symptoms may include nausea, vomiting, photophobia, (increased sensitivity to light), and phonophobia (increased sensitivity to sound). Migraines can also be associated with "auras," which are transient visual, sensory, language, or motor disturbances often manifest as flashes of colored or blinking lights that occur shortly before the onset of head pain.

Symptomatic treatment of migraine generally involves administration of triptans, such as sumatriptan or zolmitriptan, or ergot alkaloids, such as ergotamine or dihydroergotamine. While various routes of administration of these drugs for the treatment of migraine have been utilized, there still exists a need for easily administrable, fast-acting drug formulations and treatments for the amelioration of migraine symptoms.

3. SUMMARY OF THE INVENTION

The inventive embodiments provided in this Summary of the Invention are meant to be illustrative only and to provide an overview of selective embodiments disclosed herein. The Summary of the Invention, being illustrative and selective, does not limit the scope of any claim, does not provide the entire scope of inventive embodiments disclosed or contemplated herein, and should not be construed as limiting or constraining the scope of this disclosure or any claimed inventive embodiment.

The pharmacokinetic data disclosed herein (e.g., $C_{max}$, $T_{max}$, $AUC_{0-t}$, $AUC_{0-480}$ minutes, $AUC_{0-inf}$, $T_{1/2}$) can be measured from a primate, preferably a monkey, and preferably a Cynomolgus monkey, after a powder formulation disclosed herein is administered. Alternatively, the pharmacokinetic data disclosed herein (e.g., $C_{max}$, $T_{max}$, $AUC_{0-t}$, $AUC_{0-480}$ minutes, $AUC_{0-inf}$, $T_{1/2}$) can be measured from a human subject after a powder formulation disclosed herein is administered.

Presented herein are powder formulations comprising dihydroergotamine (DHE), or a pharmaceutically acceptable salt thereof. In addition to such formulations, also presented herein are methods comprising intranasally administering powder formulations comprising dihydroergotamine, or a pharmaceutically acceptable salt thereof. In some cases, the formulation is not a liquid solution or a liquid spray formulation.

The presented methods can be used for treating headache, for example, for rapid onset treatment of headache, including migraine, e.g. acute treatment of migraine with or without aura.

The presented formulations can comprise a) dihydroergotamine (DHE) or a pharmaceutically acceptable salt thereof, wherein the total dose of DHE administered is 0.1-10.0 mg; b) a microcrystalline cellulose comprises at least 15% of the total weight of the formulation. In some cases, a mean $T_{max}$ of DHE after administration of the powder formulation is about 1-120 minutes. The presented methods can comprise: intranasally administering to a human a powder formulation comprising: a) dihydroergotamine (DHE) or a pharmaceutically acceptable salt thereof, wherein the total dose of DHE administered is 0.1-10.0 mg; b) a microcrystalline cellulose comprises at least 15% of the total weight of the formulation.

The presented formulations and methods may further comprise at least one of the following: a) wherein a mean $T_{max}$ of DHE after administration of the powder formulation is about 1 to about 120 minutes; b) wherein a $(AUC_{0-30\ min}/AUC_{0-inf})\times 100\%$ of DHE after administration of the powder formulation is greater than 2.5%; c) wherein a $(AUC_{0-30\ min}/AUC_{0-inf})\times 100\%$ of DHE after administration of the powder formulation is greater than 2.5% to 25%; d) wherein a $(AUC_{0-60\ min}/AUC_{0-inf})\times 100\%$ of DHE after administration of the powder formulation is greater than 10%; e) wherein a $(AUC_{0-60\ min}/AUC_{0-inf})\times 100\%$ of DHE after administration of the powder formulation is greater than 10% to 45%; 0 wherein a $(AUC_{0-120\ min}/AUC_{0-inf})\times 100\%$ of DHE after administration of the powder formulation is greater than 25%; g) wherein a $(AUC_{0-120\ min}/AUC_{0-inf})\times 100\%$ of DHE after administration of the powder formulation is greater than 25% to 75%; h) wherein when the powder formulation is administered to a primate, preferably a monkey, and preferably a Cynomolgus monkey, a $(AUC_{0-30\ min}/AUC_{0-inf})\times 100\%$ is greater than 10%; i) wherein when the powder formulation is administered to a primate, preferably a monkey, and preferably a Cynomolgus monkey, a $(AUC_{0-60\ min}/AUC_{0-inf})\times 100\%$ is greater than 20%; j) wherein when the powder formulation is administered to a primate, preferably a monkey, and preferably a Cynomolgus monkey, a $(AUC_{0-120\ min}/AUC_{0-inf})\times 100\%$ is greater than 40%. The mean $T_{max}$ after administration of the powder formulation can be measured from a primate, preferably a monkey, and preferably a Cynomolgus monkey.

In some embodiments, a $(AUC_{0-30\ min}/AUC_{0-inf})\times 100\%$ of DHE after administration of the powder formulation is greater than 2.5%, for example, greater than 2.5%, 5%, 6%, 7%, 8%, 9%, 10%, 15%, 20%, 25%, or 30%. In some embodiments, the $(AUC_{0-30\ min}/AUC_{0-inf})\times 100\%$ of DHE after administration of the powder formulation is greater than 2.5% to 75%, for example, 2.5% to 50%, 2.5% to 25%, 2.5% to 15%, or 2.5% to 5%. In some embodiments, a $(AUC_{0-60\ min}/AUC_{0-inf})\times 100\%$ of DHE after administration of the powder formulation is greater than 5%, for example, greater than 5%, 6%, 7%, 8%, 9%, 10%, 15%, 20%, 25%, 30%, 35%, 40%, 45%, 50%, 55%, or 60%. In some embodiments, the $(AUC_{0-60\ min}/AUC_{0-inf})\times 100\%$ of DHE after administration of the powder formulation is greater than 5% to 75%, for example, 5% to 50%, 5% to 25%, 5% to 15%, 5% to 10%, 10% to 50%, 10% to 45%, 10% to 25%, 10% to 15%, 15% to 50%, 15% to 25%, or 25% to 50%. In some embodiments, a $(AUC_{0-120\ min}/AUC_{0-inf})\times 100\%$ of DHE after administration of the powder formulation is greater than 5%, for example, greater than 5%, 6%, 7%, 8%, 9%, 10%, 15%, 20%, 25%, 30%, 35%, 40%, 45%, 50%, 55%, 60%, 65%, 70%, or 75%. In some embodiments, the $(AUC_{0-120\ min}/AUC_{0-inf})\times 100\%$ of DHE after administration of the powder formulation is greater than 15% to 75%, for example, 15% to 75%, 15% to 50%, 15% to 25%, 25% to 75%, 25% to 50%, or 50% to 75%.

In some embodiments, when the powder formulation is administered to a primate, preferably a monkey, and preferably a Cynomolgus monkey, a $(AUC_{0\text{-}30\ min}/AUC_{0\text{-}inf})\times$ 100% of DHE after administration of the powder formulation is greater than 2.5%, for example, greater than 2.5%, 5%, 6%, 7%, 8%, 9%, 10%, 15%, 20%, 25%, or 30%. In some embodiments, the $(AUC_{0\text{-}30\ min}/AUC_{0\text{-}inf})\times 100\%$ of DHE after administration of the powder formulation is greater than 2.5% to 75%, for example, 2.5% to 50%, 2.5% to 25%, 2.5% to 15%, or 2.5% to 5%. For example, the $(AUC_{0\text{-}30\ min}/AUC_{0\text{-}inf})\times 100\%$ of DHE after administration of the powder formulation is about 10%. In some embodiments, when the powder formulation is administered to a primate, preferably a monkey, and preferably a Cynomolgus monkey, a $(AUC_{0\text{-}60\ min}/AUC_{0\text{-}inf})\times 100\%$ of DHE after administration of the powder formulation is greater than 5%, for example, greater than 5%, 6%, 7%, 8%, 9%, 10%, 15%, 20%, 25%, 30%, 35%, 40%, 45%, 50%, 55%, or 60%. In some embodiments, the $(AUC_{0\text{-}60\ min}/AUC_{0\text{-}inf})\times 100\%$ of DHE after administration of the powder formulation is greater than 5% to 75%, for example, 5% to 50%, 5% to 25%, 5% to 15%, 5% to 10%, 10% to 50%, 10% to 45%, 10% to 25%, 10% to 15%, 15% to 50%, 15% to 25%, or 25% to 50%. For example, the $(AUC_{0\text{-}60\ min}/AUC_{0\text{-}inf})\times$ 100% of DHE after administration of the powder formulation is about 20%. In some embodiments, when the powder formulation is administered to a primate, preferably a monkey, and preferably a Cynomolgus monkey, a $(AUC_{0\text{-}120\ min}/AUC_{0\text{-}inf})\times 100\%$ of DHE after administration of the powder formulation is greater than 5%, for example, greater than 5%, 6%, 7%, 8%, 9%, 10%, 15%, 20%, 25%, 30%, 35%, 40%, 45%, 50%, 55%, 60%, 65%, 70%, or 75%. In some embodiments, the $(AUC_{0\text{-}120\ min}/AUC_{0\text{-}inf})\times 100\%$ of DHE after administration of the powder formulation is greater than 15% to 75%, for example, 15% to 75%, 15% to 50%, 15% to 25%, 25% to 75%, 25% to 50%, or 50% to 75%. For example, the $(AUC_{0\text{-}120\ min}/AUC_{0\text{-}inf})\times 100\%$ of DHE after administration of the powder formulation is about 40%.

The presented formulations can comprise a) dihydroergotamine (DHE) or a pharmaceutically acceptable salt thereof, wherein the total dose of DHE administered is 0.1-10.0 mg; b) a microcrystalline cellulose comprises at least 15% of the total weight of the formulation. In some cases, a mean $T_{max}$ of DHE after administration of the powder formulation is about 1-120 minutes. The presented methods can comprise: intranasally administering to a human a powder formulation comprising: a) dihydroergotamine (DHE) or a pharmaceutically acceptable salt thereof, wherein the total dose of DHE administered is 0.1-10.0 mg; b) a microcrystalline cellulose comprises at least 15% of the total weight of the formulation; wherein a mean $T_{max}$ of DHE after administration of the powder formulation is about 1-120 minutes. The mean $T_{max}$ after administration of the powder formulation can be measured from a human subject.

In one embodiment, the methods and formulations comprise a mean $T_{max}$ of DHE after administration of the formulation of at least about 1 minutes, for example, at least about 1, 2, 3, 4, 5, 6, 7, 8, 9, 10, 11, 12, 13, 14, 15, 16, 17, 18, 19, 20, 25, 30, 35, 40, 45, 50, 60, 90, or 120 minutes. The mean $T_{max}$ of DHE after administration of the formulation can be about 1 to about 120 minutes, for example, about 1-120 minutes, about 1-90 minutes, about 1-60 minutes, about 1-50 minutes, 1-40 minutes, 1-30 minutes, 1-20 minutes, 1-10 minutes, 1-5 minutes, about 1-2 minutes, about 5-120 minutes, about 5-90 minutes, about 5-60 minutes, about 5-50 minutes, 5-40 minutes, 5-30 minutes, 5-25 minutes, 5-20 minutes, 5-10 minutes, about 10-120 minutes, about 10-90 minutes, about 10-60 minutes, about 10-50 minutes, 10-40 minutes, 10-30 minutes, 10-20 minutes, about 20-120 minutes, about 20-90 minutes, about 20-60 minutes, about 20-50 minutes, 20-40 minutes, 20-30 minutes, about 30-120 minutes, about 30-90 minutes, about 30-60 minutes, about 30-50 minutes, 30-40 minutes, about 40-120 minutes, about 40-90 minutes, about 40-60 minutes, 40-50 minutes, about 50-120 minutes, about 50-90 minutes, about 50-60 minutes, about 60-120 minutes, about 60-90 minutes, or about 90-120 minutes. The mean $T_{max}$ after administration of the powder formulation can be measured from a primate, preferably a monkey, and preferably a Cynomolgus monkey.

In another embodiment, the methods and formulations comprise a mean $T_{max}$ of DHE after administration of the formulation of at least about 1 minute, for example, at least about 1, 2, 3, 4, 5, 6, 7, 8, 9, 10, 11, 12, 13, 14, 15, 16, 17, 18, 19, 20, 25, 30, 35, 40, 45, 50, 60, 90, or 120 minutes. The mean $T_{max}$ of DHE after administration of the formulation can be about 1 to about 120 minutes, for example, about 1-120 minutes, about 1-90 minutes, about 1-60 minutes, about 1-50 minutes, 1-40 minutes, 1-30 minutes, 1-20 minutes, 1-10 minutes, 1-5 minutes, about 1-2 minutes, about 5-120 minutes, about 5-90 minutes, about 5-60 minutes, about 5-50 minutes, 5-40 minutes, 5-30 minutes, 5-25 minutes, 5-20 minutes, 5-10 minutes, about 10-120 minutes, about 10-90 minutes, about 10-60 minutes, about 10-50 minutes, 10-40 minutes, 10-30 minutes, 10-20 minutes, about 20-120 minutes, about 20-90 minutes, about 20-60 minutes, about 20-50 minutes, 20-40 minutes, 20-30 minutes, about 30-120 minutes, about 30-90 minutes, about 30-60 minutes, about 30-50 minutes, 30-40 minutes, about 40-120 minutes, about 40-90 minutes, about 40-60 minutes, 40-50 minutes, about 50-120 minutes, about 50-90 minutes, about 50-60 minutes, about 60-120 minutes, about 60-90 minutes, or about 90-120 minutes. The mean $T_{max}$ after administration of the powder formulation can be measured from a human subject.

In another embodiment, the methods and formulations comprise a mean $C_{max}$ of DHE after administration of the formulation of at least about 0.01 ng/mL, for example, at least about 0.01, 0.1, 0.2, 0.3, 0.4, 0.5, 0.6, 0.7, 0.8, 0.9, 1, 1.5, 2, 2.5, 3, 3.5, 4, 4.5, 5, 5.5, 6, 6.5, 7, 7.5, 8, 8.5, 9, 9.5, 10, 11, 12, 13, 14, 15, 16, 17, 18, 19, 20, 25, 30, 35, 40, 45, 50, 55, 60, 65, 70, 75, 80, 85, 90, 95, 100, 110, 120, 130, 140, or 150 ng/mL. The mean $C_{max}$ of DHE after administration of the formulation can be about 0.1 to about 150 ng/mL, for example, about 0.1-150, 0.1-130, 0.1-110, 0.1-90, 0.1-70, 0.1-50, 0.1-30, 0.1-10, 0.1-5, 0.1-1.0, 0.1-0.5, 1-150, 1-130, 1-110, 1-90, 1-70, 1-50, 1-30, 1-10, 1-5, 5-150, 5-130, 5-110, 5-90, 5-70, 5-50, 5-30, 5-10, 10-150, 10-130, 10-110, 10-90, 10-70, 10-50, 10-30, 30-150, 30-130, 30-110, 30-90, 30-70, 30-50, 50-150, 50-130, 50-110, 50-90, 50-70, 70-150, 70-130, 70-110, 70-90, 90-150, 90-130, 90-110, 110-150, 110-130, or 130-150 ng/mL. The mean $C_{max}$ after administration of the powder formulation can be measured from a primate, preferably a monkey, and preferably a Cynomolgus monkey.

In another embodiment, the methods and formulations comprise a mean $C_{max}$ of DHE after administration of the formulation of at least about 0.01 ng/mL, for example, at least about 0.01, 0.1, 0.2, 0.3, 0.4, 0.5, 0.6, 0.7, 0.8, 0.9, 1, 1.5, 2, 2.5, 3, 3.5, 4, 4.5, 5, 5.5, 6, 6.5, 7, 7.5, 8, 8.5, 9, 9.5, 10, 11, 12, 13, 14, 15, 16, 17, 18, 19, 20, 25, 30, 35, 40, 45, 50, 55, 60, 65, 70, 75, 80, 85, 90, 95, 100, 110, 120, 130, 140, or 150 ng/mL. The mean $C_{max}$ of DHE after administration of the formulation can be about 0.1 to about 150 ng/mL, for example, about 0.1-150, 0.1-130, 0.1-110, 0.1-90, 0.1-70, 0.1-50, 0.1-30, 0.1-10, 0.1-5, 0.1-1.0, 0.1-0.5, 1-150, 1-130, 1-110, 1-90, 1-70, 1-50, 1-30, 1-10, 1-5, 5-150, 5-130, 5-110, 5-90, 5-70, 5-50, 5-30, 5-10, 10-150, 10-130, 10-110, 10-90, 10-70, 10-50, 10-30, 30-150, 30-130, 30-110, 30-90, 30-70, 30-50, 50-150, 50-130, 50-110, 50-90, 50-70, 70-150, 70-130, 70-110, 70-90, 90-150, 90-130, 90-110, 110-150, 110-130, or 130-150 ng/mL. The mean $C_{max}$ after administration of the powder formulation can be measured from a human subject.

In another embodiment, the methods and formulations comprise a mean $AUC_{0\text{-}inf}$ of DHE after administration of the formulation of at least about 0.5 ng·h/mL, for example, at least about 0.5, 1, 2, 3, 4, 5, 6, 7, 8, 9, 10, 20, 30, 40, 50, 60, 70, 80, 90, 100, 200, 300, 400, 500, 600, or 700 ng·h/mL. The mean $AUC_{0\text{-}inf}$ of DHE after administration of the formulation can be about 0.5 to about 700 ng·h/mL, for example, about 0.5-700, 0.5-500, 0.5-300, 0.5-100, 0.5-80, 0.5-60, 0.5-40, 0.5-20, 0.5-10, 0.5-5, 0.5-2, 0.5-1, 1-700, 1-500, 1-300, 1-100, 1-80, 1-60, 1-40, 1-20, 1-10, 1-5, 10-700, 10-500, 10-300, 10-100, 10-80, 10-60, 10-40, 10-20, 20-700, 20-500, 20-300, 20-100, 20-80, 20-60, 20-40, 40-700, 40-500, 40-300, 40-100, 40-80, 40-60, 60-700, 60-500, 60-300, 60-100, 60-80, 80-700, 80-500, 80-300, 80-100, 100-700, 100-500, 100-300, 300-700, 300-500, or 500-700 ng·h/mL. The mean $AUC_{0\text{-}inf}$ after administration of the powder formulation can be measured fr from a primate, preferably a monkey, and preferably a Cynomolgus monkey.

In another embodiment, the methods and formulations comprise a mean $AUC_{0\text{-}inf}$ of DHE after administration of the formulation of at least about 0.5 ng·h/mL, for example, at least about 0.5, 1, 2, 3, 4, 5, 6, 7, 8, 9, 10, 20, 30, 40, 50, 60, 70, 80, 90, 100, 200, 300, 400, 500, 600, or 700 ng·h/mL. The mean $AUC_{0\text{-}inf}$ of DHE after administration of the formulation can be about 0.5 to about 700 ng·h/mL, for example, about 0.5-700, 0.5-500, 0.5-300, 0.5-100, 0.5-80, 0.5-60, 0.5-40, 0.5-20, 0.5-10, 0.5-5, 0.5-2, 0.5-1, 1-700, 1-500, 1-300, 1-100, 1-80, 1-60, 1-40, 1-20, 1-10, 1-5, 10-700, 10-500, 10-300, 10-100, 10-80, 10-60, 10-40, 10-20, 20-700, 20-500, 20-300, 20-100, 20-80, 20-60, 20-40, 40-700, 40-500, 40-300, 40-100, 40-80, 40-60, 60-700, 60-500, 60-300, 60-100, 60-80, 80-700, 80-500, 80-300, 80-100, 100-700, 100-500, 100-300, 300-700, 300-500, or 500-700 ng·h/mL. The mean $AUC_{0\text{-}inf}$ after administration of the powder formulation can be measured from a human subject.

In another embodiment, the methods and formulations comprise a mean $AUC_{0\text{-}t}$ of DHE after administration of the formulation of at least about 0.5 ng·h/mL, for example, at least about 0.5, 1, 2, 3, 4, 5, 6, 7, 8, 9, 10, 20, 30, 40, 50, 60, 70, 80, 90, 100, 200, 300, 400, 500, 600, or 700 ng·h/mL. The mean $AUC_{0\text{-}inf}$ of DHE after administration of the formulation can be about 0.5 to about 700 ng·h/mL, for example, about 0.5-700, 0.5-500, 0.5-300, 0.5-100, 0.5-80, 0.5-60, 0.5-40, 0.5-20, 0.5-10, 0.5-5, 0.5-2, 0.5-1, 1-700, 1-500, 1-300, 1-100, 1-80, 1-60, 1-40, 1-20, 1-10, 1-5, 10-700, 10-500, 10-300, 10-100, 10-80, 10-60, 10-40, 10-20, 20-700, 20-500, 20-300, 20-100, 20-80, 20-60, 20-40, 40-700, 40-500, 40-300, 40-100, 40-80, 40-60, 60-700, 60-500, 60-300, 60-100, 60-80, 80-700, 80-500, 80-300, 80-100, 100-700, 100-500, 100-300, 300-700, 300-500, or 500-700 ng·h/mL. The mean $AUC_{0\text{-}inf}$ after administration of the powder formulation can be measured from a primate, preferably a monkey, and preferably a Cynomolgus monkey. The measurement can be taken 5, 10, 20, 30, 60, 90, 120, 180, 240, 300, 360, 420, or 480 minutes.

In another embodiment, the methods and formulations comprise a mean $AUC_{0\text{-}t}$ of DHE after administration of the formulation of at least about 0.5 ng·h/mL, for example, at least about 0.5, 1, 2, 3, 4, 5, 6, 7, 8, 9, 10, 20, 30, 40, 50, 60, 70, 80, 90, 100, 200, 300, 400, 500, 600, or 700 ng·h/mL. The mean $AUC_{0\text{-}inf}$ of DHE after administration of the formulation can be about 0.5 to about 700 ng·h/mL, for example, about 0.5-700, 0.5-500, 0.5-300, 0.5-100, 0.5-80, 0.5-60, 0.5-40, 0.5-20, 0.5-10, 0.5-5, 0.5-2, 0.5-1, 1-700, 1-500, 1-300, 1-100, 1-80, 1-60, 1-40, 1-20, 1-10, 1-5, 10-700, 10-500, 10-300, 10-100, 10-80, 10-60, 10-40, 10-20, 20-700, 20-500, 20-300, 20-100, 20-80, 20-60, 20-40, 40-700, 40-500, 40-300, 40-100, 40-80, 40-60, 60-700, 60-500, 60-300, 60-100, 60-80, 80-700, 80-500, 80-300, 80-100, 100-700, 100-500, 100-300, 300-700, 300-500, or 500-700 ng·h/mL. The mean $AUC_{0\text{-}inf}$ after administration of the powder formulation can be measured from a human subject. The measurement can be taken 5, 10, 20, 30, 60, 90, 120, 180, 240, 300, 360, 420, or 480 minutes.

In another embodiment, the methods and formulations comprise a mean $T_{1/2}$ of DHE after administration of the formulation of at least about 10 minutes, for example, at least about 10, 20, 30, 40, 50, 60, 70, 80, 90, 100, 120, 150, 200, 250, or 300 minutes. The mean $T_{1/2}$ of DHE after administration of the formulation can be about 10 to about 300 minutes, for example, about 10-300, 10-250, 10-200, 10-150, 10-120, 10-100, 10-80, 10-60, 10-40, 10-20, 20-300, 20-250, 20-200, 20-150, 20-120, 20-100, 20-80, 20-60, 20-40, 40-300, 40-250, 40-200, 40-150, 40-120, 40-100, 40-80, 40-60, 60-300, 60-250, 60-200, 60-150, 60-120, 60-100, 60-80, 80-300, 80-250, 80-200, 80-150, 80-120, 80-100, 100-300, 100-250, 100-200, 100-150, 100-120, 120-300, 120-250, 120-200, 120-150, 150-300, 150-250, 150-200, 200-300, 200-250, or 250-300 minutes. For example, the mean $T_{1/2}$ of DHE after administration of the formulation is about 100 to about 300 minutes. The mean $T_{1/2}$ after administration of the powder formulation can be measured from a monkey (e.g., Cynomolgus monkeys).

In another embodiment, the methods and formulations comprise a mean $T_{1/2}$ of DHE after administration of the formulation of at least about 10 minutes, for example, at least about 10, 20, 30, 40, 50, 60, 70, 80, 90, 100, 120, 150, 200, 250, or 300 minutes. The mean $T_{1/2}$ of DHE after administration of the formulation can be about 10 to about 300 minutes, for example, about 10-300, 10-250, 10-200, 10-150, 10-120, 10-100, 10-80, 10-60, 10-40, 10-20, 20-300, 20-250, 20-200, 20-150, 20-120, 20-100, 20-80, 20-60, 20-40, 40-300, 40-250, 40-200, 40-150, 40-120, 40-100, 40-80, 40-60, 60-300, 60-250, 60-200, 60-150, 60-120, 60-100, 60-80, 80-300, 80-250, 80-200, 80-150, 80-120, 80-100, 100-300, 100-250, 100-200, 100-150, 100-120, 120-300, 120-250, 120-200, 120-150, 150-300, 150-250, 150-200, 200-300, 200-250, or 250-300 minutes. For example, the mean $T_{1/2}$ of DHE after administration of the formulation is about 100 to about 300 minutes. The mean $T_{1/2}$ after administration of the powder formulation can be measured from a human subject.

In another aspect, the methods presented herein comprising intranasally administering to a human a powder formulation comprising dihydroergotamine (DHE) or a pharmaceutically acceptable salt thereof wherein the method further comprises at least one of the following: wherein a mean $T_{max}$ of DHE after administration of the formulation is about 2 to about 50 minutes; b) wherein a mean $C_{max}$ of DHE after administration of the formulation is about 0.1 to about 150 ng/mL; c) wherein a mean $AUC_{0\text{-}inf}$ of DHE after administration of the formulation is about 1 to about 700 ng·h/mL; d) wherein a mean $T_{1/2}$ of DHE after administration of the formulation is about 100 to about 300 minutes. In one embodiment, the mean $T_{max}$ of DHE after administration of the formulation is about 2 to about 50 minutes. In another embodiment, the mean $C_{max}$ of DHE after administration of the formulation is about 0.1 to about 150 ng/mL. In another embodiment, the mean $AUC_{0\text{-}inf}$ of DHE after administration of the formulation is about 1 to about 700 ng·h/mL. In another embodiment, the mean $T_{1/2}$ of DHE after administration of the formulation is about 100 to about 300 minutes. The mean $T_{max}$, $C_{max}$, $AUC_{0\text{-}inf}$, and/or $T_{1/2}$ after administration of the powder formulation can be measured from a primate, preferably a monkey, and preferably a Cynomolgus monkey.

In another aspect, the methods presented herein comprising intranasally administering to a human a powder formulation comprising dihydroergotamine (DHE) or a pharmaceutically acceptable salt thereof wherein the method further comprises at least one of the following: wherein a mean $T_{max}$ of DHE after administration of the formulation is about 2 to about 50 minutes; b) wherein a mean $C_{max}$ of DHE after administration of the formulation is about 0.1 to about 150 ng/mL; c) wherein a mean $AUC_{0\text{-}inf}$ of DHE after administration of the formulation is about 1 to about 700 ng·h/mL; d) wherein a mean $T_{1/2}$ of DHE after administration of the formulation is about 100 to about 300 minutes. In one embodiment, the mean $T_{max}$ of DHE after administration of the formulation is about 2 to about 50 minutes. In another embodiment, the mean $C_{max}$ of DHE after administration of the formulation is about 0.1 to about 150 ng/mL. In another embodiment, the mean $AUC_{0\text{-}inf}$ of DHE after administration of the formulation is about 1 to about 700 ng·h/mL. In another embodiment, the mean $T_{1/2}$ of DHE after administration of the formulation is about 100 to about 300 minutes. The mean $T_{max}$, $C_{max}$, $AUC_{0\text{-}inf}$, and/or $T_{1/2}$ after administration of the powder formulation can be measured from a human subject.

In one case, the mean $T_{max}$ of DHE is about 10 to about 30 minutes, the mean $C_{max}$ of DHE is about 0.5 to about 6 ng/mL, the mean $AUC_{0\text{-}inf}$ of DHE is about 1 to about 15 ng·h/mL, and the mean $T_{1/2}$ of DHE is about 100 to about 300 minutes. In another case, the mean $T_{max}$ of DHE is about 10 to about 50 minutes, the mean $C_{max}$ of DHE is about 1 to about 15 ng/mL, the mean $AUC_{0\text{-}inf}$ of DHE is about 10 to about 50 ng·h/mL, and the mean $T_{1/2}$ of DHE is about 100 to about 300 minutes. In another case, the mean $T_{max}$ of DHE is about 10 to about 50 minutes, the mean $C_{max}$ of DHE is about 2 to about 20 ng/mL, the mean $AUC_{0\text{-}inf}$ of DHE is about 15 to about 110 ng·h/mL, and the mean $T_{1/2}$ of DHE is about 100 to about 300 minutes. In another case, the mean $T_{max}$ of DHE is about 10 to about 50 minutes, the mean $C_{max}$ of DHE is about 2 to about 50 ng/mL, the mean $AUC_{0\text{-}inf}$ of DHE is about 15 to about 200 ng·h/mL, and the mean $T_{1/2}$ of DHE is about 100 to about 300 minutes. The mean $T_{max}$, $C_{max}$, $AUC_{0\text{-}inf}$, and/or $T_{1/2}$ after administration of the powder formulation can be measured from a primate, preferably a monkey, and preferably a Cynomolgus monkey.

In one case, the mean $T_{max}$ of DHE is about 10 to about 30 minutes, the mean $C_{max}$ of DHE is about 0.5 to about 6 ng/mL, the mean $AUC_{0\text{-}inf}$ of DHE is about 1 to about 15 ng·h/mL, and the mean $T_{1/2}$ of DHE is about 100 to about 300 minutes. In another case, the mean $T_{max}$ of DHE is about 10 to about 50 minutes, the mean $C_{max}$ of DHE is about 1 to about 15 ng/mL, the mean $AUC_{0\text{-}inf}$ of DHE is about 10 to about 50 ng·h/mL, and the mean $T_{1/2}$ of DHE is about 100 to about 300 minutes. In another case, the mean $T_{max}$ of DHE is about 10 to about 50 minutes, the mean $C_{max}$ of DHE is about 2 to about 20 ng/mL, the mean $AUC_{0\text{-}inf}$ of DHE is about 15 to about 110 ng·h/mL, and the mean $T_{1/2}$ of DHE is about 100 to about 300 minutes. In another case, the mean $T_{max}$ of DHE is about 10 to about 50 minutes, the mean $C_{max}$ of DHE is about 2 to about 50 ng/mL, the mean $AUC_{0\text{-}inf}$ of DHE is about 15 to about 200 ng·h/mL, and the mean $T_{1/2}$ of DHE is about 100 to about 300 minutes. The mean $T_{max}$, $C_{max}$, $AUC_{0\text{-}inf}$, and/or $T_{1/2}$ after administration of the powder formulation can be measured from a human subject.

In some cases, the powder formulation is administered such that the intersubject variability in DHE $C_{max}$ is less than 30%. For example, the intersubject variability in DHE $C_{max}$ is less than 30%, 25%, 20%, 15%, 10%, or 5%. In some cases, the powder formulation is administered such that the intersubject variability in DHE $T_{max}$ is less than 30%. For example, the intersubject variability in DHE $T_{max}$ is less than 30%, 25%, 20%, 15%, 10%, or 5%. In some cases, the powder formulation is administered such that the intersubject variability in DHE $AUC_{0\text{-}inf}$ is less than 30%. For example, the intersubject variability in DHE $AUC_{0\text{-}inf}$ is less than 30%, 25%, 20%, 15%, 10%, or 5%. In some cases, the powder formulation is administered such that the intersubject variability in DHE $T_{1/2}$ is less than 30%. For example, the intersubject variability in DHE $T_{1/2}$ is less than 30%, 25%, 20%, 15%, 10%, or 5%. The intersubject variability in DHE $T_{max}$, $C_{max}$, $AUC_{0\text{-}inf}$, and/or $T_{1/2}$ after administration of the powder formulation can be measured from primates, preferably monkeys, and preferably a Cynomolgus monkeys.

In some cases, the powder formulation is administered such that the intersubject variability in DHE $C_{max}$ is less than 30%. For example, the intersubject variability in DHE $C_{max}$ is less than 30%, 25%, 20%, 15%, 10%, or 5%. In some cases, the powder formulation is administered such that the intersubject variability in DHE $T_{max}$ is less than 30%. For example, the intersubject variability in DHE $T_{max}$ is less than 30%, 25%, 20%, 15%, 10%, or 5%. In some cases, the powder formulation is administered such that the intersubject variability in DHE $AUC_{0\text{-}inf}$ is less than 30%. For example, the intersubject variability in DHE $AUC_{0\text{-}inf}$ is less than 30%, 25%, 20%, 15%, 10%, or 5%. In some cases, the powder formulation is administered such that the intersubject variability in DHE $T_{1/2}$ is less than 30%. For example, the intersubject variability in DHE $T_{1/2}$ is less than 30%, 25%, 20%, 15%, 10%, or 5%. The intersubject variability in DHE $T_{max}$, $C_{max}$, $AUC_{0\text{-}inf}$, and/or $T_{1/2}$ after administration of the powder formulation can be measured from human subjects.

In another embodiment, the powder formulation comprises DHE mesylate. For example, the powder formulation comprises DHE mesylate, microcrystalline cellulose, and tribasic calcium phosphate.

The methods and formulations may further comprise a microcrystalline cellulose component with a mean particle size diameter of about 100 μm or less. The microcrystalline cellulose component may have a mean particle size diameter of less than about 100 μm, for example, about 95, 90, 85, 80, 75, 70, 65, 60, 55, 50, 45, 40, 35, 30, 25, 20, 15, 10, 5 μm or less.

The microcrystalline cellulose component may comprise a first microcrystalline cellulose portion with a mean particle diameter size of about 30 μm or less, and a second microcrystalline cellulose portion with a mean particle size diameter of about 30 to about 100 μm. The first microcrystalline cellulose portion may have a mean particle diameter size of about 30 μm or less, for example, 30-25, 30-20, 30-15, 30-10, 30-5, 25-20, 25-15, 25-10, 25-5, 20-15, 20-10, 20-5, 15-10, 15-5 or 10-5 μm. In a specific embodiment, the first microcrystalline cellulose portion has a mean particle diameter size of about 15-30 μm. In another specific embodiment, the first microcrystalline cellulose portion has a mean particle diameter size of about 18-20 μm. In yet another specific embodiment, the first microcrystalline cellulose portion has a mean particle diameter size of about 20 μm. The second microcrystalline cellulose portion may have a mean particle diameter size of about 30 to about 100 μm, for example, 30-90, 30-80, 30-70, 30-60, 30-50, 30-40, 40-90, 40-80, 40-70, 40-60, 40-50, 50-90, 50-80, 50-70, 50-60, 60-90, 60-80, 60-70, 70-90, 70-80, or 80-90 μm. In a specific embodiment, the second microcrystalline cellulose portion has a mean particle diameter size of about 45-65 μm. In another specific embodiment, the second microcrystalline cellulose portion has a mean particle diameter size of about 45-55 μm. In another specific embodiment, the second microcrystalline cellulose portion has a mean particle diameter size of about 50-55 μm. In yet another specific embodiment, the second microcrystalline cellulose portion has a mean particle diameter size of about 50 μm.

In one embodiment, the first microcrystalline cellulose portion has a mean particle diameter size of about 15 to about 30 μm and the second microcrystalline cellulose portion has a mean particle diameter size of about 45 to about 65 μm. In another embodiment, the first microcrystalline cellulose portion has a mean particle size of about 20 μm and the second microcrystalline cellulose portion has a mean particle size diameter of about 50 to about 55 μm. In yet another embodiment, the first microcrystalline cellulose portion has a mean particle diameter size of about 20 μm, and the second microcrystalline cellulose portion has a mean particle size diameter of about 50 μm. In some cases, the microcrystalline cellulose component is substantially free of particles with a mean particle diameter size of about 31 to about 44 μm. The method of claim 4, wherein the microcrystalline cellulose component is substantially free of particles with a mean particle diameter size of about 31 to about 49 μm. In some cases, substantially free of particles with a mean particle diameter size means less than 15%, 10%, 5%, or 2% of all the particles fall into the given range.

In another aspect, the microcrystalline cellulose component may comprise at least about 5% of the total weight of the powder formulation, for example, at least about 5%, 6%, 7%, 8%, 9%, 10%, 15%, 20%, 25%, 30%, 35%, 40%, 45%, 50%, 55%, 60%, 65%, 70%, 75%, 80%, 85%, 90%, 95% or 95% of the total weight of the powder formulation. The microcrystalline cellulose component may comprise about 15% to about 99% of the total weight of the powder formulation, for example, about 15%-99%, 20%-99%, 30%-99%, 40-99%, 50-99%, 60-99%, 70-99%, 80-99%, 90-99%, 15%-90%, 20%-90%, 30%-90%, 40-90%, 50-90%, 60-90%, 70-90%, 80-90%, 15%-80%, 20%-80%, 30%-80%, 40-80%, 50-80%, 60-80%, 70-80%, 15%-70%, 20%-70%, 30%-70%, 40-70%, 50-70%, 60-70%, 15%-60%, 20%-60%, 30%-60%, 40-60%, 50-60%, 15%-50%, 20%-50%, 30%-50%, 40-50%, 15%-40%, 20%-40%, 30%-40%, 15%-30%, 20%-30%, or 15-20% of the total weight of the powder formulation.

In one embodiment, the first microcrystalline cellulose component comprises about 10 to about 90% of the total weight of the powder formulation, for example, about 10%-90%, 15%-90%, 20%-90%, 30%-90%, 40-90%, 50-90%, 60-90%, 70-90%, 80-90%, 10%-80%, 15%-80%, 20%-80%, 30%-80%, 40-80%, 50-80%, 60-80%, 70-80%, 10%-70%, 15%-70%, 20%-70%, 30%-70%, 40-70%, 50-70%, 60-70%, 10%-60%, 15%-60%, 20%-60%, 30%-60%, 40-60%, 50-60%, 10%-50%, 15%-50%, 20%-50%, 30%-50%, 40-50%, 10%-40%, 15%-40%, 20%-40%, 30%-40%, 10%-30%, 15%-30%, 20%-30%, 10%-20%, 15-20%, or 10%-15% of the total weight of the powder formulation. In one embodiment, the first microcrystalline cellulose component comprises about 70% to about 90% of the total weight of the powder formulation. In another embodiment, the first microcrystalline cellulose component comprises about 70% to about 90% of the total weight of the powder formulation.

In one embodiment, the second microcrystalline cellulose component comprises about 5% to about 15% of the total weight of the powder formulation, for example, about 5%-15%, 5%-10%, or 10%-15% of the total weight of the powder formulation. In one embodiment, the second microcrystalline cellulose component comprises about 10% of the total weight of the powder formulation. For example, in particular embodiments, the first microcrystalline cellulose portion comprises about 8% to about 90% of the total weight of the formulation, and the second microcrystalline cellulose portion comprises about 10% of the total weight of the formulation. In another certain embodiment, the first microcrystalline cellulose portion is about 5% to about 90% of the total weight of the powder formulation, and the second microcrystalline portion is about 10% of the total weight of the powder formulation.

In another aspect, the methods and formulations may further comprise a fluidizing agent. For example, the fluidizing agent is tribasic calcium phosphate. The tribasic calcium phosphate can be about 0.1% to about 5.0% of the total weight of the powder formulation, for example about 0.1%-5%, 0.1%-4%, 0.1%-3%, 0.1%-2%, 0.1%-1%, 0.1%-0.5%, 0.5%-5%, 0.5%-4%, 0.5%-3%, 0.5%-2%, 0.5%-1%, 1%-5%, 1%-4%, 1%-3%, 1%-2%, 2%-5%, 2%-4%, 2%-3%, 3%-5%, 3%-4%, or 4%-5% of the total weight of the powder formulation. In one embodiment, the tribasic calcium phosphate is about 0.5% to about 1.0% of the total weight of the powder formulation. In another embodiment, the tribasic calcium phosphate is about 0.5% to about 1.5% of the total weight of the powder formulation. In another embodiment, the tribasic calcium phosphate is about 0.8% of the total weight of the powder formulation.

In another aspect, the methods and formulations may further comprise at least one of the following: an adenosine receptor antagonist, a phosphodiesterase inhibitor, an acetylcholinesterase inhibitor, a vasodilator, xanthine, caffeine, paraxanthine, theobromine, and theophylline. For example, the methods and formulations further comprise caffeine. The caffeine can be at least about 1% of the total weight of the powder formulation, for example about 1%, 2%, 3%, 4%, 5%, 6%, 7%, 8%, 9%, 10%, 15%, 20%, 25%, 30%, 35%, 40%, 45%, 50%, 55%, 60% or more of the total weight of the powder formulation. The caffeine can be about 1% to 60% of the total weight of the powder formulation, for example, about 1%-60%, 1%-50%, 1%-40%, 1%-30%, 1%-20%, 1%-10%, 1%-5%, 10%-60%, 10%-50%, 10%-40%, 10%-30%, 10%-20%, 20%-60%, 20%-50%, 20%-40%, 20%-30%, 30%-60%, 30%-50%, 30%-40%, 40%-60%, 40%-50%, or 50%-60% of the total weight of the powder formulation. In another embodiment, the powder formulation comprises about 5% to 10% caffeine. In a particular embodiment, the caffeine is anhydrous caffeine. In another embodiment, the powder formulation comprises about 10% to 15% caffeine.

In another aspect, a total dose of the powder formulation administered can be at least about 0.1 mg, for example, at least about 0.1, 0.2, 0.3, 0.4, 0.5, 0.6, 0.7, 0.8, 0.9, 1, 1.5, 2, 2.5, 3, 3.5, 4, 4.5, 5, 5.5, 6, 6.5, 7, 7.5, 8, 8.5, 9, 9.5, 10, 11, 12, 13, 14, 15, 16, 17, 18, 19, 20, or 25 mg. The total dose of the powder formulation administered can be about 0.1 to about 25 mg, for example, about 0.1-25.0 mg, about 0.1-20.0 mg, about 0.1-15.0 mg, about 0.1-10.0 mg, about 0.1-5.0 mg, about 0.1-2.0 mg, about 0.1-1.0 mg, about 0.1-0.5 mg, about 0.2-25.0 mg, about 0.2-20.0 mg, about 0.2-15.0 mg, about 0.2-10.0 mg, about 0.2-5.0 mg, about 0.2-2.0 mg, about 0.2-1.0 mg, about 0.2-0.5 mg, about 0.5-25.0 mg, about 0.5-20.0 mg, about 0.5-15.0 mg, about 0.5-10.0 mg, about 0.5-5.0 mg, about 0.5-2.0 mg, about 0.5-1.0 mg, about 1.0-25.0 mg, about 1.0-20.0 mg, about 1.0-15.0 mg, about 1.0-10.0 mg, about 1.0-5.0 mg, about 1.0-2.0 mg, about 2.0-25.0 mg, about 2.0-20.0 mg, about 2.0-15.0 mg, about 2.0-10.0 mg, about 2.0-5.0 mg, about 5.0-25.0 mg, about 5.0-20.0 mg, about 5.0-15.0 mg, about 5.0-10.0 mg, about 10.0-25.0 mg, about 10.0-20.0 mg, about 10.0-15.0 mg, about 15.0-25.0 mg, or about 15.0-20.0 mg. For example, the total dose of the powder formulation administered is about 25 mg.

In another aspect, the powder formulation comprises a total dose of DHE administered of at least about 0.1 mg, for example, at least about 0.1, 0.2, 0.3, 0.4, 0.5, 0.6, 0.7, 0.8, 0.9, 1, 1.5, 2, 2.5, 3, 3.5, 4, 4.5, 5, 5.5, 6, 6.5, 7, 7.5, 8, 8.5, 9, 9.5, or 10 mg. The powder formulation may comprise a total dose of DHE administered of about 0.1 to about 10.0 mg, for example, about 0.1-10.0 mg, about 0.1-9.0 mg DHE, about 0.1-8.0 mg DHE, about 0.1-7.0 mg DHE, about 0.1-6.0 mg DHE, about 0.1-5.0 mg, about 0.1-4.0 mg DHE, about 0.1-3.0 mg DHE, about 0.1-2.0 mg, about 0.1-1.0 mg, about 0.1-0.5 mg, about 0.2-10.0 mg, about 0.2-9.0 mg DHE, about 0.2-8.0 mg DHE, about 0.2-7.0 mg DHE, about 0.2-6.0 mg DHE, about 0.2-5.0 mg, about 0.2-4.0 mg DHE, about 0.2-3.0 mg DHE, about 0.2-2.0 mg, about 0.2-1.0 mg, about 0.2-0.5 mg, about 0.5-10.0 mg, about 0.5-9.0 mg DHE, about 0.5-8.0 mg DHE, about 0.5-7.0 mg DHE, about 0.5-6.0 mg DHE, about 0.5-5.0 mg, about 0.5-4.0 mg DHE, about 0.5-3.0 mg DHE, about 0.5-2.0 mg, about 0.5-1.0 mg, about 1.0-10.0 mg, about 1.0-5.0 mg, about 1.0-4.0 mg DHE, about 1.0-3.0 mg DHE, about 1.0-2.0 mg, about 2.0-10.0 mg, about 2.0-9.0 mg DHE, about 2.0-8.0 mg DHE, about 2.0-7.0 mg DHE, about 2.0-6.0 mg DHE, about 2.0-5.0 mg, about 2.0-4.0 mg DHE, about 2.0-3.0 mg DHE, about 5.0-10.0 mg, about 5.0-9.0 mg DHE, about 5.0-8.0 mg DHE, about 5.0-7.0 mg DHE, about 5.0-6.0 mg DHE, about 6.0-10.0 mg, about 6.0-9.0 mg DHE, about 6.0-8.0 mg DHE, about 6.0-7.0 mg DHE, about 7.0-10.0 mg, about 7.0-9.0 mg DHE, about 7.0-8.0 mg DHE, about 8.0-10.0 mg, about 8.0-9.0 mg DHE, or about 9.0-10.0 mg DHE. For example, the total dose of DHE administered of about 0.5 mg. In certain embodiments, the total dose of DHE administered is 0.1-5.0 mg. In certain other embodiments, the total amount of DHE administered is 0.5-5.0 mg. In certain other embodiments, the total amount of DHE administered is 0.5-3.0 mg. In certain other embodiments, the total amount of DHE administered is 1.0-2.0 mg.

In some embodiments, the powder formulation has an angle of repose about 53° or less, for example, about 53°, 52°, 51°, 50°, 48°, 46°, 44°, 42°, 40°, 38°, 36°, 34°, 32°, 30°, 280°, 26°, 24°, 22°, 20° or less.

Presented herein are methods and formulations used for treating headache. For example, the methods and formulations are used for treating migraine. In some cases, the methods of treating migraine are methods for the acute treatment of migraine headaches with or without aura.

In one embodiment, at least a portion of the powder formulation is administered to a single nostril of the human. In another embodiment, at least a portion of the powder formulation is administered to each nostril of the human. For example, in a specific embodiment of the method, about half of the formulation is administered to one nostril and about half of the formulation is administered to the other nostril of the human.

4. BRIEF DESCRIPTION OF DRAWINGS

FIG. 1 presents pharmacokinetic profiles of DHE intranasal powder formulations, including comparisons with Migranal nasal spray, in monkey.

Figure 2:
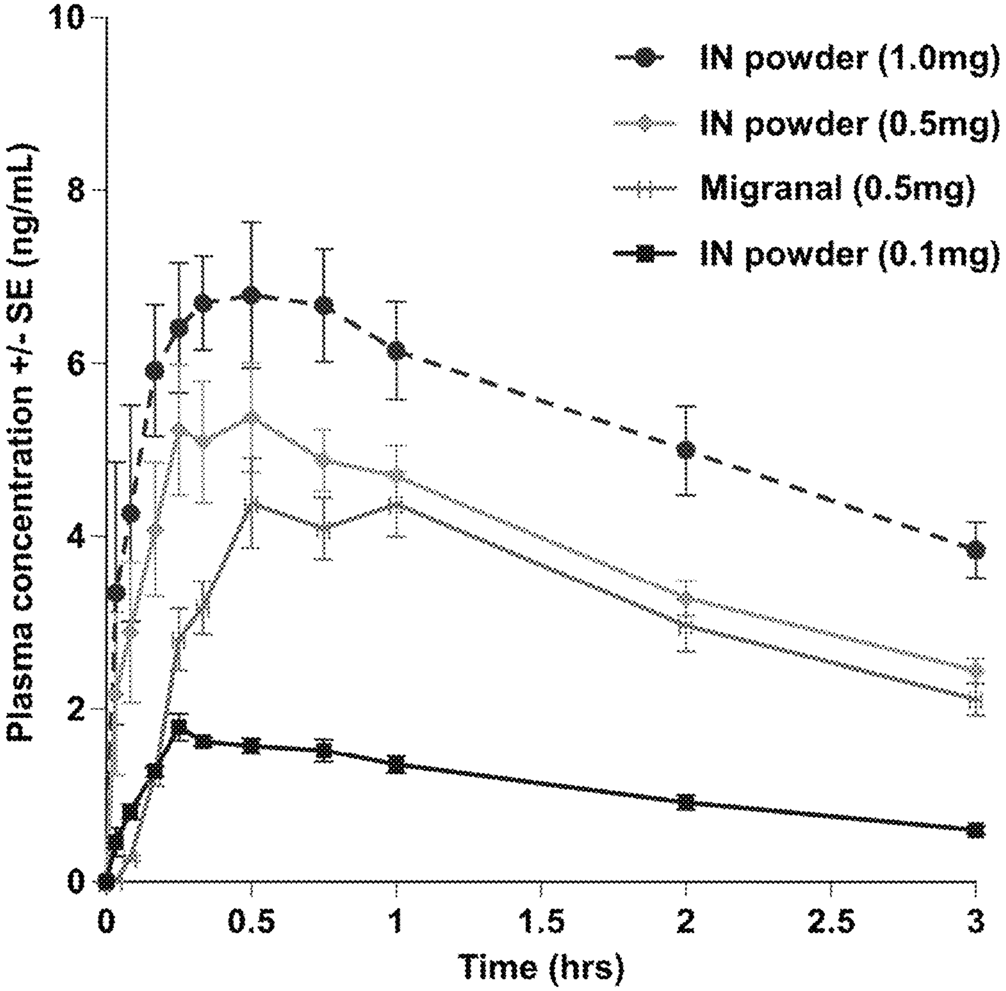

FIG. 2 presents pharmacokinetic profiles of DHE intranasal powder formulations, including comparisons with Migranal nasal spray, in monkey from 0 to 3 hours.

Figure 3:
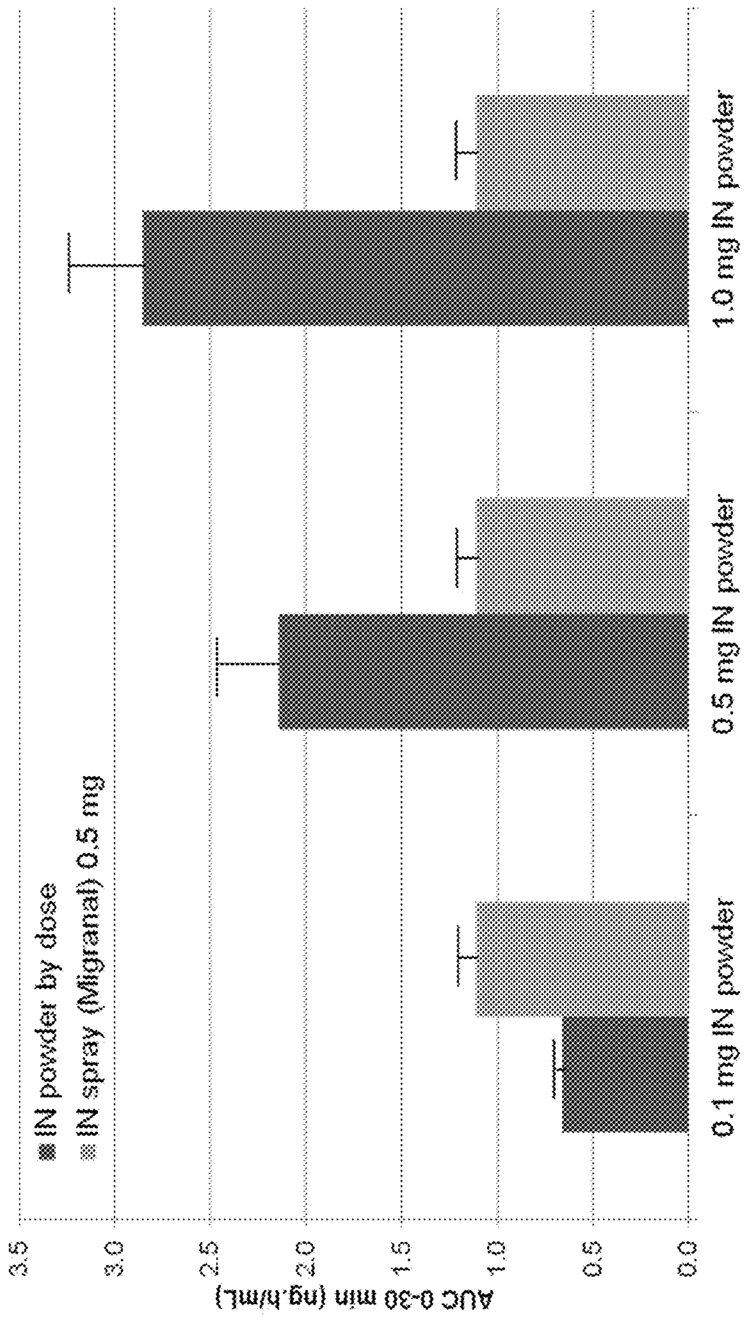

FIG. 3 presents a comparison of DHE intranasal powder formulations and Migranal nasal spray AUC from 0-30 minutes.

Figure 4:
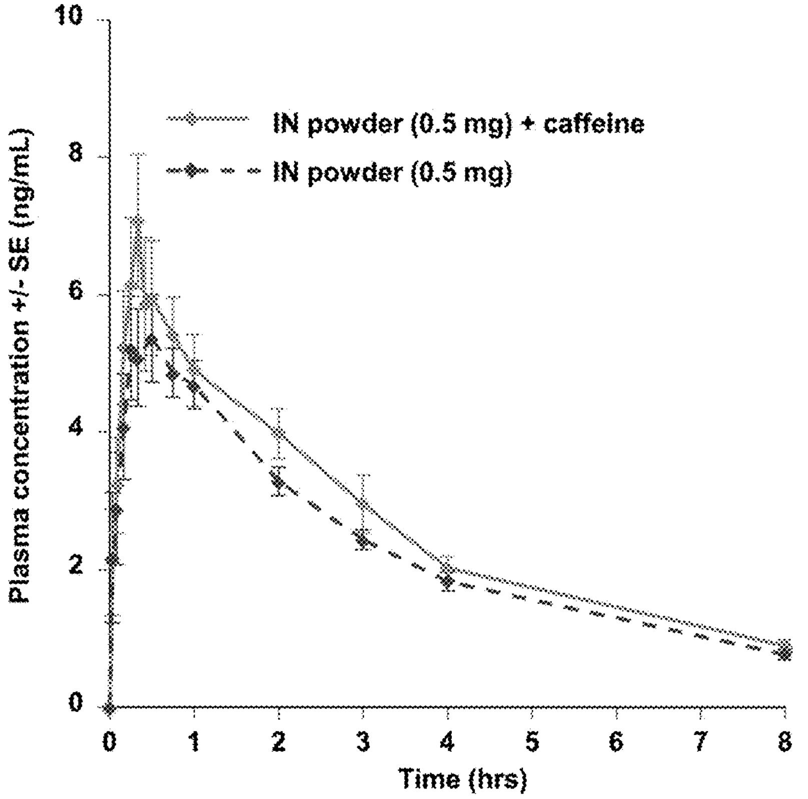

FIG. 4 presents pharmacokinetic profiles of caffeine vs. non-caffeine containing DHE intranasal powder formulations (0.5 mg DHE dose).

Figure 5:
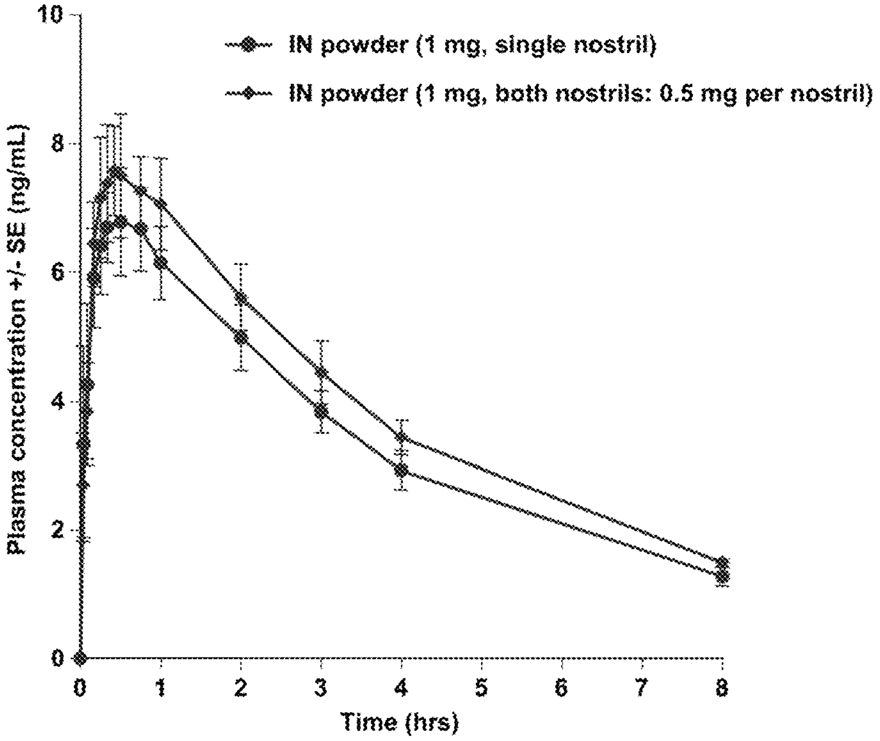

FIG. 5 presents pharmacokinetic profiles of 1 mg DHE powder formulation administered to a single nostril vs. 1 mg DHE powder formulation administered to both nostrils ("double nostril"; 0.5 mg DHE dose/nostril).

Figure 6:
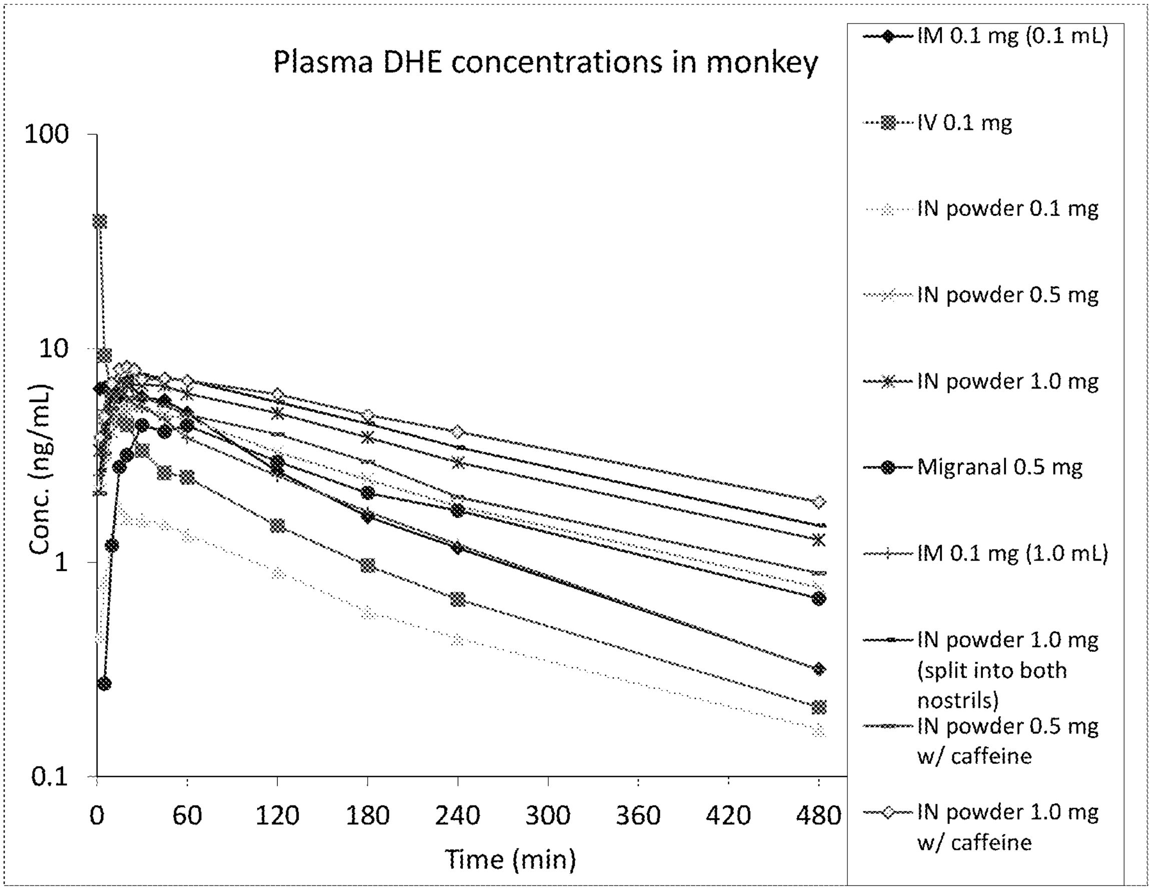

FIG. 6 represents plasma DHE concentrations in monkeys over 480 minutes after the tested administrations.

5. DETAILED DESCRIPTION

Unless defined otherwise, all technical and scientific terms used herein have the same meaning as commonly understood by one of the ordinary skill in the art to which this invention belongs. Although any methods and materials similar or equivalent to those described herein can be used in the practice or testing of the formulations or unit doses herein, some methods and materials are now described. Unless mentioned otherwise, the techniques employed or contemplated herein are standard methodologies. The materials, methods and examples are illustrative only and not limiting.

The details of one or more inventive embodiments are set forth in the accompanying drawings, the claims, and the description herein. Other features, objects, and advantages of the inventive embodiments disclosed and contemplated herein can be combined with any other embodiment unless explicitly excluded.

Unless otherwise indicated, open terms for example "contain," "containing," "include," "including," and the like mean comprising.

The singular forms "a", "an", and "the" are used herein to include plural references unless the context clearly dictates otherwise. Accordingly, unless the contrary is indicated, the numerical parameters set forth in this application are approximations that may vary depending upon the desired properties sought to be obtained by the present invention.

Unless otherwise indicated, some embodiments herein contemplate numerical ranges. When a numerical range is provided, unless otherwise indicated, the range includes the range endpoints. Unless otherwise indicated, numerical ranges include all values and subranges therein as if explicitly written out. Unless otherwise indicated, any numerical ranges and/or values herein can be at 80-125% of the numerical ranges and/or values.

Unless otherwise indicated, "mean particle diameter" can refer to the particle size distribution of a powder in its non-aggregated state. Primary particle diameter can be determined using a laser-diffraction particle size distribution analyzer. In some embodiments, the particle size analyzer can be Mastersizer 2000 manufactured by Malvern Instruments Limited.

The pharmacokinetic data disclosed herein (e.g., $C_{max}$, $T_{max}$, $AUC_{0-t}$, $AUC_{0-480}$ minutes, $AUC_{0-inf}$, $T_{1/2}$) can be measured from a primate, preferably a monkey, and preferably a Cynomolgus monkey, after a powder formulation disclosed herein is administered. Alternatively, the pharmacokinetic data disclosed herein (e.g., $C_{max}$, $T_{max}$, $AUC_{0-t}$, $AUC_{0-480}$ minutes, $AUC_{0-inf}$, $T_{1/2}$) can be measured from a human subject after a powder formulation disclosed herein is administered.

Presented herein are formulations comprising dihydroergotamine (DHE), or a pharmaceutically acceptable salt thereof. Also presented herein are methods for treating headache, for example, methods of treating migraine in a subject, e.g. in a human, comprising intranasally administering particular formulations comprising dihydroergotamine, or a pharmaceutically acceptable salt thereof, to a subject, e.g. a human, having a headache, for example, a migraine, wherein the formulation is not a liquid solution or a liquid spray formulation. For example, presented herein are methods for rapid onset treatment of headache, including migraine, e.g. acute treatment of migraine with or without aura, comprising intranasally administering the formulations presented herein. Unless noted, such formulations are referred to herein as powder formulations.

Intranasal administration, as used herein in the context of the powder formulations presented herein, unless otherwise noted, refers to administration whereby at least 95±5% of the powder formulation is administered to the nasal cavity as measured by multiple path particle dosimetry (MPPD) model analysis, a computational model used to estimate human airway particle dosimetry (see, e.g., Anjilvel, S. and Asgharian, B. (1995) Fundam. Appl. Toxicol. 28, 41-50; and National Institute for Public Health and the Environment (RIVM) (2002) Multiple Path Particle Dosimetry Model (MPPD v 1.0): A Model for Human and Rat Airway Particle Dosimetry. Bilthoven, The Netherlands. RIVA Report 650010030), or via an Andersen Cascade Impactor.

Generally, not less than 90% of the particles in the powder formulations presented herein have a diameter less than 150 μm, and not more than 5% of the particles in the powder formulations have a diameter less than 10 μm. In addition, generally, the overall mean particle size of the particles in the powder formulations presented herein about 15 to about 30 μm, about 18 to about 25 μm, about 18 to about 20 μm, or about 20 μm.

In a particular aspect, presented herein is a method of treating headache, for example treating migraine e.g., a method for acute treatment of migraine with or without aura, comprising intranasally administering to a human having a headache, e.g., a migraine, a formulation comprising DHE, or a pharmaceutically acceptable salt thereof, e.g., DHE mesylate, microcrystalline cellulose, and tribasic calcium phosphate, wherein the formulation is not a liquid solution or a liquid spray formulation. Unless noted, such formulations are referred to herein as powder formulations. In a specific aspect, provided herein are methods of treating headache, including migraine, comprising intranasally administering powder formulations comprising dihydroergotamine or a pharmaceutically acceptable salt thereof, e.g., dihydroergotamine mesylate, microcrystalline cellulose with a mean particle diameter size of about 100 μm or less, and tribasic calcium phosphate. Throughout, unless otherwise noted, "about" means within ±10% of a value. For example, if it is stated that a component makes up "about 70%" of a mixture, it is implied that the component makes up within a range of 63% and 77% of the mixture. In addition, in instances wherein "about" is used, it is to be understood that embodiments involving the exact value associated with "about" are also contemplated. For example, when an embodiment recites "about 0.5 mg DHE," an embodiment reciting "0.5 mg DHE" is also contemplated and is described herein.

In yet another aspect, provided herein are methods of treating headache, including migraine, comprising intranasally administering powder formulations comprising dihydroergotamine or a pharmaceutically acceptable salt thereof, e.g., dihydroergotamine mesylate, a microcrystalline cellulose portion with a mean particle size diameter of about 50-55 μm, e.g., 50 μm, comprising about 10% of the total weight of the powder formulation, a microcrystalline cellulose portion with a mean particle size of about 20 μm comprising about 3 to about 90%, e.g., 8 to about 90%, of the total weight of the powder formulation and, optionally, a fluidizing agent. In certain embodiments, the powder formulations utilized as part of the methods further comprise caffeine, e.g., anhydrous caffeine. Throughout, unless otherwise noted, percent (%) weight, in the context of the powder formulations presented herein, refers to weight per weight percent (%) (W/W %).

In another aspect, presented herein are powder formulations that can be utilized in conjunction with the methods of treating headache, including migraine. In a certain aspect, presented herein are powder formulations comprising dihydroergotamine or a pharmaceutically acceptable salt thereof. In a specific aspect, provided herein are powder formulations comprising: a) dihydroergotamine or a pharmaceutically acceptable salt thereof, e.g., dihydroergotamine mesylate; b) microcrystalline cellulose, e.g., a microcrystalline cellulose with a mean particle diameter size of about 100 μm or less; and c) tribasic calcium phosphate. In yet another aspect, provided herein are powder formulations comprising dihydroergotamine, or a pharmaceutically acceptable salt thereof, e.g., dihydroergotamine mesylate a microcrystalline cellulose portion with a mean particle size diameter of about 50-55 μm, e.g., 50 μm, comprising about 10% of the total weight of the powder formulation, a microcrystalline cellulose portion with a mean particle size of about 20 μm comprising about 3% to about 90%, e.g., about 8 to about 90%, of the total weight of the powder formulation and, optionally, a fluidizing agent. In certain embodiments, the powder formulations further comprise caffeine, e.g., anhydrous caffeine.

In certain embodiments, greater than or equal to about 90% of the particles in the powder formulation have a diameter less than 150 μm. In other embodiments the overall mean particle size of the formulation is about 15 to about 30 μm, about 18 to about 25 μm, about 18 to about 20 μm, or about 20 μm. In further embodiments, less than or equal to about 5% of the particles in the powder formulation have a diameter less than 10 μm. In yet other embodiments, greater than or equal to about 90% of the particles in the power formulation have a diameter less than 150 μm; and the overall mean particle size of the formulation is about 15 to about 30 μm, about 18 to about 25 μm, about 18 to about 20 μm, or about 20 μm; and less than or equal to about 5% of the particles in the powder formulation have a diameter less than 10 μm.

5.1 Dihydroergotamine

Dihydroergotamine (DHE) is an ergot alkaloid having a structure as follows:

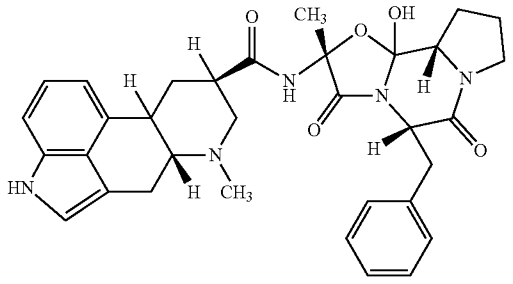

The methods and formulations presented herein can utilize DHE and any pharmaceutically acceptable salt, hydrate, polymorph, isomer, diastereomer, prodrug, metabolite, ion pair complex, or chelate thereof.

In certain embodiments, the methods and formulations presented herein comprise a pharmaceutically acceptable salt of DHE. In embodiments wherein a pharmaceutically acceptable salt of DHE is utilized, the pharmaceutically acceptable salt of DHE may be used instead of or in addition to DHE in any or all of the methods and compositions presented herein.

A pharmaceutically acceptable salt of DHE can be formed using a pharmaceutically acceptable non-toxic acid or base, including an inorganic acid or base, or an organic acid or base. In specific embodiments, a pharmaceutically acceptable salt of DHE that can be utilized in connection with the methods and formulations presented herein is a pharmaceutically acceptable salt derived from acids including, but not limited to, the following: acetic, alginic, anthranilic, benzenesulfonic, benzoic, camphorsulfonic, citric, ethenesulfonic, formic, fumaric, furoic, galacturonic, gluconic, glucuronic, glutamic, glycolic, hydrobromic, hydrochloric, isethionic, lactic, maleic, malic, mandelic, methanesulfonic, mucic, nitric, pamoic, pantothenic, phenylacetic, phosphoric, propionic, salicylic, stearic, succinic, sulfanilic, sulfuric, tartaric acid, or p-toluenesulfonic acid. In one embodiment the pharmaceutically acceptable salt of DHE is a salt of methanesulfonic acid. An alternative nomenclature of the methanesulfonic acid salt of DHE is DHE mesylate.

For further description of pharmaceutically acceptable salts that can be used in the methods described herein see, for example, S. M. Barge et al., “Pharmaceutical Salts,” 1977, J. Pharm. Sci. 66:1-19, which is incorporated herein by reference in its entirety.

The mean particle size of the DHE or pharmaceutically acceptable salt of DHE, e.g, DHE mesylate, utilized can be less than about 100 μm, for example, about 95, 90, 85, 80, 75, 70, 65, 60, 55, 50, 45, 40, 35, 30, 25, 20, 15, 10, 5 μm or less. The mean particle size of the DHE or pharmaceutically acceptable salt of DHE, e.g, DHE mesylate, utilized can be about 5-100 μm, for example, for example, about 5-90, 5-80, 5-70, 5-60, 5-50, 5-40, 5-30, 5-20, 5-10, 10-90, 10-80, 10-70, 10-60, 10-50, 10-40, 10-30, 10-20, 20-90, 20-80, 20-70, 20-60, 20-50, 20-40, 20-30,30-90, 30-80, 30-70, 30-60, 30-50, 30-40, 40-90, 40-80, 40-70, 40-60, 40-50, 50-90, 50-80, 50-70, 50-60, 60-90, 60-80, 60-70, 70-90, 70-80, or 80-90 μm. The mean particle size of the DHE or pharmaceutically acceptable salt of DHE, e.g, DHE mesylate, utilized can be about 5.0, 5.5, 6.0, 6.5, 7.0, 7.5, 8.0, 8.5, 9.0, 9.5, 10, 11, 12, 13, 14, 15, 16, 17, 18, 19, 20, 25, 30, 35, 40, 45, 50, 55, 60, 65, 70, 75, 80, 85, 90, 95, or 100 μm. Moreover, generally, not less than 90% of the DHE or pharmaceutically acceptable salt of DHE, e.g., DHE mesylate, particles in the powder formulations presented herein have a diameter less than 150 μm, and not more than 5% of the particles in the powder formulation have a diameter less than 5 μm. In addition, generally, the overall mean particle size of the DHE particles in the powder formulations presented herein about 15 to about 30 μm, about 18 to about 25 μm, about 18 to about 20 μm, or about 20 μm.

In some embodiments, the total weight of the powder formulation comprises about 0.4 to about 46%, or about 0.4 to about 23% or about 0.4 to about 9%, or about 2 to about 9%, or about 4 to about 9% of DHE. In other embodiments, the total weight of the powder formulation comprises about 0.3 to about 37%, or about 0.3 to about 18% or about 0.3 to about 7%, or about 2 to about 7%, or about 3 to about 9% of DHE or a pharmaceutically acceptable salt thereof.

5.2 Methods of Treating Headache

Presented herein are methods for treating headache, for example, methods of treating migraine in a subject, e.g. in a human, comprising intranasally administering particular formulations comprising dihydroergotamine, or a pharmaceutically acceptable salt thereof, to a subject, e.g. a human, having a headache, for example, a migraine. For example, presented herein are methods for rapid onset treatment of headache, including migraine, e.g. acute treatment of migraine with or without aura, comprising intranasally administering the formulations presented herein.

In a particular aspect, provided herein are methods of treating headache, including migraine, comprising intranasally administering powder formulations comprising dihydroergotamine or a pharmaceutically acceptable salt thereof. In a specific aspect, provided herein are methods of treating headache, including migraine, comprising intranasally administering powder formulations comprising dihydroergotamine or a pharmaceutically acceptable salt thereof, e.g., dihydroergotamine mesylate, microcrystalline cellulose with a mean particle diameter size of about 100 μm or less, and tribasic calcium phosphate. In yet another aspect, provided herein are methods of treating headache, including migraine, comprising intranasally administering powder formulations comprising dihydroergotamine or a pharmaceutically acceptable salt thereof, e.g., dihydroergotamine mesylate a microcrystalline cellulose portion with a mean particle size diameter of about 50-55 μm, e.g., about 50 μm, comprising about 10% of the total weight of the powder formulation, a microcrystalline cellulose portion with a mean particle size of about 20 μm comprising about 3 to about 90%, e.g., about 8 to about 90%, of the total weight of the powder formulation and, optionally, a fluidizing agent. In certain embodiments, the powder formulations utilized as part of the methods further comprise caffeine, e.g., anhydrous caffeine.

In certain embodiments, the headache treated by the methods provided herein is a cluster headache, chronic daily headache, or migraine, including adult migraine or pediatric migraine. The migraine can be migraine with aura or migraine without aura. In particular embodiments, the methods presented herein are methods for acute treatment of a human having a migraine with or without aura. In other embodiments, the methods presented herein are methods for chronic treatment of migraine with or without aura.

"Treating," as used herein, refers to the amelioration of at least one symptom of the disorder being treated. Thus, the methods of treating headache, for example migraine, presented herein ameliorate at least one symptom of the headache, for example migraine. In certain embodiments, the methods of treating headache, for example migraine, presented herein reduce at least one symptom of the headache, for example migraine. In other embodiments, the methods of treating headache, for example migraine, presented herein eliminate at least one symptom of the headache, for example, migraine.

Symptoms of headache, e.g., cluster headache, chronic daily headache or migraine, include pain. Symptoms of migraine can also include, for example, nausea, vomiting, photophobia, phonophobia, osmophobia (aversion to, or hypersensitivity to, odors), vertigo, and/or allodynia. In certain embodiments, the methods of treating headache, for example migraine, presented herein ameliorate at least one such symptom of the headache, for example migraine. In particular embodiments, the methods of treating headache, for example migraine, presented herein reduce at least one such symptom of the headache, for example migraine. In other particular embodiments, the methods of treating headache, for example migraine, presented herein eliminate at least one such symptom of the headache, for example, migraine.

In specific embodiments, the methods of treating migraine ameliorate at least one of pain, nausea, phonophobia or photophobia. In other specific embodiments, such methods ameliorate at least two, three or all four of said symptoms.

In some embodiments, the headache has a severity of more than about any of 1, 2, 3, 4, 5, 6, 7, 8, 9, or 10 on a scale of 0 to 10. In certain embodiments, the methods of treating a headache, for example migraine, presented herein ameliorate at least one symptom of a headache, for example a migraine, having a severity of more than about any of 1, 2, 3, 4, 5, 6, 7, 8, 9, or 10 on a scale of 0 to 10. In certain embodiments, the methods of treating headache, for example migraine, presented herein reduce the severity of a headache, for example a migraine, having a severity of more than about any of 1, 2, 3, 4, 5, 6, 7, 8, 9, or 10 on a scale of 0 to 10.

In certain embodiments, the intensity of headache pain, for example, pain associated with migraine, can be measured according to a 4-point severity scale (0=no pain, 1=mild, 2=moderate, 3=severe). In certain embodiments, the methods of treating headache, for example migraine, presented herein reduce the severity of headache pain, for example pain associated with migraine, by at least one point on such a 4-point severity scale.

In certain embodiments, the methods of treating migraine presented herein ameliorate at least one symptom of the migraine, e.g., ameliorate at least one of pain, nausea, phonophobia, or photophobia. The symptom or symptoms can, for example, be evaluated via a four point severity scale as follows: 0=none 1=mild symptom, not interfering with normal daily activities 2=moderate symptom, causing some restriction to normal activities 3=severe, leading to inability to perform normal daily activities. Alternatively, or additionally, a symptom or symptoms, including the four listed above, can be evaluated via a four-point functional disability scale that assesses the level of impairment a symptom has on a patient's ability to perform usual daily activities, as follows: 0=not at all impaired 1=slightly impaired 2=moderately impaired 3=severely or completely impaired See, Cephalalgia 1991; 11:1-12.

In certain embodiments, the methods of treating headache, for example migraine, presented herein ameliorate at least one symptom of the headache, for example migraine, within 10, 15, 20, 25, 30 or 45 minutes of intranasally administering a powder formulation presented herein. In other embodiments, the methods of treating headache, for example migraine, presented herein ameliorate at least one symptom of the headache, for example migraine, within 1, 1.5, 2, 2.5, 3, or 4 hours of intranasally administering a powder formulation presented herein. In particular embodiments, methods of treating headache, for example migraine, presented herein the amelioration of at least one symptom of the headache, for example migraine, is sustained for about 3, 4, 5, 6, 8, 12, 18, 36, or 48 hours.

With respect to the microcrystalline cellulose component of the powder formulations presented herein, generally, acceptable microcrystalline cellulose can include microcrystalline cellulose obtained by decomposing cellulose materials such as pulp by either or both of acid and alkaline hydrolyses, then purifying the hydrolysate, and crushing or grinding it before, during, or after drying. Microcrystalline cellulose of particular mean particle diameter size can be obtained, for example, via appropriate processing, e.g., via fine grinding using a high-speed rotary impact mill or air attrition mill as necessary, and size sorting. In certain embodiments, microcrystalline cellulose components utilized as part of the microcellulose of the powder formulations presented herein can include products available under the trade names of Ceolus®PH-F20JP, Ceolus®PH-301, Ceolus®PH-101, Ceolus®PH-102, and Ceolus®PH-302 (available from Asahi Kasei Corporation), and Avicel®PH-105, Avicel®PH-101, Avicel®PH-102, Avicel®PH-301, and Avicel®PH-302 (available from FMC Biopolymer Corporation). In a particular embodiment, powder formulations that can be used in conjunction with the methods and compositions presented herein can comprise Ceolus®PH-F20JP and Ceolus®PH-301.

Mean particle size diameters, for example, the mean particle size diameters of the microcrystalline portions of the powder formulations described herein, can be determined using standard techniques, for example, via a laser-diffraction particle size distribution analyzer or via sorting methods. The mean particle diameter size refers to a diameter that divides particles into two groups of equal numbers: a group with greater diameters and a group with smaller diameters. The mean diameter size determined using a laser-diffraction particle size distribution analyzer corresponds to 50% volume in a determined cumulative particle size distribution curve. The mean particle diameter size can, for example, be determined by a sorting method that corresponds to 50 (W/W) % on a cumulative particle size distribution curve that can be obtained by sorting an appropriate amount of the particle being assessed, for an appropriate time, e.g., ten minutes, on an electromagnetic sieve shaker, using standard sieves and weighing the sample remaining on each sieve.

With respect to tribasic calcium phosphate (also known as hydroxyapatite), any pharmaceutically acceptable tribasic calcium phosphate can be used in conjunction with the methods and compositions presented herein. In certain embodiments, the tribasic calcium phosphate utilized has an average particle diameter of about 10-100 μm, for example, about 10 to 75 μm, about 10 to 50 μm, about 10-30 μm, or about 10 μm. Moreover, generally, not less than 90% of the tribasic calcium phosphate particles in the powder formulations presented herein have a diameter less than 150 μm, and not more than 5% of the particles in the powder formulation have a diameter less than 10 μm. In addition, generally, the overall mean particle size of the tribasic calcium phosphate particles in the powder formulations presented herein about 15 to about 30 μm, about 18 to about 25 μm, about 18 to about 20 μm, or about 20 μm.

In certain embodiments, greater than or equal to about 90% of the tribasic calcium phosphate particles have a diameter less than 150 μm. In other embodiments the overall mean particle size of the tribasic calcium phosphate particles is about 15 to about 30 μm, about 18 to about 25 μm, about 18 to about 20 μm, or about 20 μm. In further embodiments, less than or equal to about 5% of the tribasic calcium phosphate particles have a diameter less than 10 μm. In yet other embodiments, for the tribasic calcium phosphate particles, greater than or equal to about 90% of the particles have a diameter less than 150 μm; and the overall mean particle size is about 15 to about 30 μm, about 18 to about 25 μm, about 18 to about 20 μm, or about 20 μm; and less than or equal to about 5% of the particles have a diameter less than 10 μm.

The powder formulations described herein can be made using standard techniques. For example, the components of the powder formulations can be mixed while applying a shearing force, e.g., via a high shear mixer/stirrer. Alternatively, for example, the components of the powder formulations can be homogeneously mixed using, e.g., a mortar or V-blender. The order of mixing is not critical to the production process. See Example 1, below, for representative, non-limited examples of methods for the production of powder formulations as presented herein.

The powder formulations can be intranasally administered utilizing any techniques known in the art. For example, the formulations can be administered utilizing a dispenser, for example a single use dispenser or a multi-use dispenser. In certain embodiments the powder formulations are administered using a device such as, for example, a device as described in US 2011/0045088 or in WO 2012/105236, each of which is incorporated herein by reference for its disclosure of devices that can be utilized to intranasally administer powder formulations to a primate, for example, to a human. In specific embodiments, the device used to administer the powder formulation is a Fit-lizer™ (SNBL, LTD) intranasal dispenser device.

In certain specific embodiments, the powder formulations presented herein are encapsulated prior to administration. For example, the powder formulations presented herein can be encapsulated in unit dose form. In certain embodiments, the encapsulated powder formulations are released from the capsule prior to administration. In other embodiments, the powder formulations are released from the capsule upon administration. Powder formulations can, for example, be intranasally administered utilizing devices designed to accept and delivery powder formulations that have been encapsulated. In certain embodiments, the fill weight of the capsule comprises an appropriate excess amount of the powder formulation such that the desired dose is administered, taking into account the particular administration device being utilized.

In one aspect, presented herein is a method of treating headache comprising: intranasally administering to a human having a headache a powder formulation comprising: a) DHE, or a pharmaceutically acceptable salt thereof, wherein the total dose of DHE being administered is about 0.1-10.0 mg; b) a microcrystalline cellulose component with a mean particle size diameter of about 100 μm or less; and c) tribasic calcium phosphate. Herein, unless otherwise noted, "the total dose of DHE being administered" and like phrasing means the total amount of parent DHE in the DHE form, e.g., amount of DHE free base in a pharmaceutically acceptable DHE salt, being administered. In a particular embodiment, the powder formulation comprises DHE mesylate, and the total amount of DHE free base of the DHE mesylate being administered is about 0.1-10.0 mg.

In certain embodiments of such a method, the powder formulation is administered to a single nostril of the human having a headache. In other embodiments of the method, a portion of the powder formulation is administered to each nostril of the human. For example, in a specific embodiment of the method, about half of the powder formulation is administered to one nostril and about half of the powder formulation is administered to the other nostril of the human having a headache.

In another aspect, presented herein is a method of treating migraine comprising: intranasally administering to a human having a migraine a powder formulation comprising: a) DHE, or a pharmaceutically acceptable salt thereof, wherein the total dose of DHE being administered is about 0.1-10.0 mg; b) a microcrystalline cellulose component with a mean particle size diameter of about 100 μm or less; and c) tribasic calcium phosphate. In a particular embodiment, the powder formulation comprises DHE mesylate. In certain embodiments of the method, the powder formulation is administered to a single nostril of the human having a migraine. In other embodiments of the method, a portion of the powder formulation is administered to each nostril of the human having a migraine. For example, in a specific embodiment, about half of the powder formulation is administered to one nostril and about half of the powder formulation is administered to the other nostril of the human having a migraine.

In yet another embodiment of such a method of treating headache, including migraine, the microcrystalline cellulose component of the formulation comprises a first microcrystalline cellulose portion with a mean particle diameter size of about 30 μm or less, and a second microcrystalline cellulose portion with a mean particle size diameter of about 30-100 μm. In a particular embodiment of such a method, the first microcrystalline cellulose portion has a mean particle diameter size of about 15-30 μm. In a specific embodiment of such a method, the first microcrystalline cellulose portion has a mean particle diameter size of about 18-20 μm. In yet another specific embodiment of such a method, the first microcrystalline cellulose portion has a mean particle diameter size of about 20 μm. In another particular embodiment of such a method, the second microcrystalline cellulose portion has a mean particle diameter size of about 45-65 μm. In a specific embodiment of such a method, the second microcrystalline cellulose portion has a mean particle diameter size of about 45-55 μm. In another specific embodiment of such a method, the second microcrystalline cellulose portion has a mean particle diameter size of about 50-55 μm. In another specific embodiment of such a method, the second microcrystalline cellulose portion has a mean particle diameter size of about 50 μm. In yet another embodiment of such a method, the first microcrystalline cellulose portion has a mean particle diameter size of about 20 μm, and the second microcrystalline cellulose portion has a mean particle size diameter of about 50 μm. In yet other embodiments of such a method, the first microcrystalline cellulose portion has a mean particle diameter size of about 30 μm or less, for example, about 15-30 μm, about 18-20 μm, or about 20 lam, and the second microcrystalline cellulose portion has a mean particle diameter size of about 45-65 lam, about 45-55 μm, about 50-55 μm, or about 50 μm. In instances wherein the method is a method for treating migraine, the method can, in certain embodiments, be a method for the acute treatment of migraine with or without aura.

In certain embodiments of such methods of treating headache, including migraine, the microcrystalline cellulose component of the powder formulation comprises about 10 to about 99%, e.g., about 15 to about 99%, of the total weight of the formulation. In other embodiments, the microcrystalline cellulose component of the powder formulation comprises about 53 to about 99%, about 76 to about 99%, about 76 to about 97%, about 90 to about 97%, or about 90 to about 95% of the total weight of the formulation. In some embodiments, the microcrystalline cellulose component of the powder formulation comprises about 10 to about 98%, about 18 to about 98%, about 18 to about 91%, about 67 to about 91%, or about 67 to about 83%. In further embodiments, the microcrystalline cellulose component of the powder formulation comprises about 53%, about 76%, about 90%, about 95%, about 97%, or about 99% of the total weight of the formulation. In other embodiments, the microcrystalline cellulose component of the powder formulation comprises about 10%, about 18%, about 66%, about 83%, about 91%, or about 98% of the total weight of the formulation.

For example, in particular embodiments, the first microcrystalline cellulose portion comprises about 3.0 to about 90%, e.g., about 8.0 to about 90%, of the total weight of the formulation, and the second microcrystalline cellulose portion comprises about 10% of the total weight of the formulation. In other embodiments, the first microcrystalline cellulose portion comprises about comprises about 43 to about 89%, about 66 to about 89%, about 66 to about 87%, about 80 to about 87%, or about 80 to about 85% of the total weight of the formulation, of the total weight of the formulation, and the second microcrystalline cellulose portion comprises about 10% of the total weight of the formulation. In some embodiments, the microcrystalline cellulose component of the powder formulation comprises about 1 to about 88%, about 8 to about 88%, about 8 to about 81%, about 57 to about 81%, or about 57 to about 83%, and the second microcrystalline cellulose portion comprises about 10% of the total weight of the formulation. In further embodiments, the microcrystalline cellulose component of the powder formulation comprises about 43%, about 66%, about 80%, about 85%, about 87%, or about 89% of the total weight of the formulation, and the second microcrystalline cellulose portion comprises about 10% of the total weight of the formulation. In other embodiments, the microcrystalline cellulose component of the powder formulation comprises about 1%, about 8%, about 57%, about 73%, about 81%, or about 88% of the total weight of the formulation, and the second microcrystalline cellulose portion comprises about 10% of the total weight of the formulation.

In certain embodiments of the methods of treating headache, including migraine, the tribasic calcium phosphate comprises about 0.5-1.0% of the total weight of the formulation. In specific embodiments of the methods of treating headache, including migraine, the tribasic calcium phosphate comprises about 0.8% of the total weight of the formulation.

In another aspect, the powder formulations utilized as part of the methods of treating headache, including migraine, further comprise caffeine, for example, anhydrous caffeine In specific embodiments, the powder formulations utilized as part of the methods of treating headache, including migraine, comprise about 1-60%, about 1-25%, about 10-60%, or about 10-25% caffeine, for example, anhydrous caffeine. In other embodiments, the powder formulations utilized as part of the methods of treating headache, including migraine, comprise about 1%, about 5%, about 6%, about 10%, about 12%, about 20%, about 23%, about 39%, about 48%, about 50%, or about 58% caffeine.

While the particle size of the caffeine utilized as part of the powder formulations described herein is not particularly critical, the mean particle size of the caffeine, e.g., anhydrous caffeine, is generally about 10-100 μm, for example, about 10 to 75 μm, about 10 to 50 μm, about 10-30 μm, about 10-20 μm, about 15-20 μm, about 10 μm, about 15 μm, about 16 μm, about 17 μm, about 18 μm, about 19 μm, or about 20 μm. Moreover, generally, not less than 90% of the caffeine, e.g., anhydrous caffeine, particles in the powder formulations presented herein have a diameter less than 150 μm, and not more than 5% of the caffeine particles in the powder formulation have a diameter less than 10 μm. In addition, generally, the overall mean particle size of the caffeine, e.g., anhydrous caffeine, particles in the powder formulations presented herein about 15 to about 30 μm, about 18 to about 25 μm, about 18 to about 20 μm, or about 20 μm.

In particular embodiments of such methods of treating headache, including migraine, the total dose of DHE administered is about 0.1-5.0 mg. In certain other embodiments, the total dose of DHE administered is about 0.5-5.0 mg. In certain other embodiments, the total dose of DHE administered is about 0.5-3.0 mg. In certain other embodiments, the total dose of DHE administered is about 1.0-2.0 mg. In particular embodiments of such methods, the total dose of DHE administered is about 0.1 mg, about 0.5 mg, about 1.0 mg, about 1.5 mg, about 2.0 mg, about 3.0 mg, about 4.0 mg, about 5.0 mg, about 7.5 mg, or about 10.0 mg. In certain embodiments, the total dose is administered into a single nostril. In other embodiments, a portion of the total dose is administered into each nostril. In yet other embodiments, about half of the total dose is administered into one nostril and the remaining half is administered into the other nostril.

In specific embodiments of such a method of treating headache, including migraine, the total amount of the powder formulation administered is 5, 10, 15, 20, 25, 30, 35, 40, 45, or 50 mg. In certain embodiments, the total amount of the powder formulation is administered into a single nostril. In other embodiments, a portion of the total amount of the powder formulation is administered into each nostril. In yet other embodiments, about half of the total amount of the powder formulation is administered into one nostril and the remaining half is administered into the other nostril.

In particular embodiments wherein such methods of treating headache are methods of treating migraine, the methods can include a method for the acute treatment of migraine with or without aura.

In certain embodiments, the methods of treating headache, including migraine, comprise administering the powder formulation such that the mean $T_{max}$ of DHE is about 10-50 minutes. In other embodiments, the mean $T_{max}$ of DHE is about 10-30 minutes. In further embodiments, the mean $T_{max}$ of DHE is about 5-50 minutes. In yet further embodiments, the mean $T_{max}$ of DHE is about 5-30 minutes. In further embodiments, the mean $T_{max}$ of DHE is about 2-50 minutes. In yet further embodiments, the mean $T_{max}$ of DHE is about 2-30 minutes. In other embodiments, the methods of treating headache, including migraine, comprise administering the powder formulation such that the mean $C_{max}$ of DHE is about 0.5-100 ng/mL. In yet other embodiments, such methods of treating headache, including migraine, utilizing about 0.1-1.0 mg DHE comprise administering the powder formulation such that the mean $AUC_{0\text{-}inf}$ of DHE is about 1-500 ng·h/mL. In further embodiments, the mean $AUC_{0-30\ min}$ of DHE is about 1-500 ng·h/mL. In yet other embodiments, the methods of treating headache, including migraine, comprise administering the powder formulation such that the mean $T_{1/2}$ of DHE is about 110-260 minutes. In yet other embodiments, the methods of treating headache, including migraine, comprise administering the intersubject variability in DHE $C_{max}$ is less than 30%.

In a particular aspect, presented herein is a method of treating headache, including migraine, comprising: intranasally administering to a human having a headache, e.g., migraine, a powder formulation comprising: a) DHE, or a pharmaceutically acceptable salt thereof, wherein the total dose of DHE being administered is about 0.1-2.0 mg; b) a microcrystalline cellulose component comprising a first microcrystalline cellulose portion with a mean particle size of about 30 μm or less, for example, about 15-30 μm, about 18-20 μm, or about 20 μm, and a second microcrystalline cellulose portion with a mean particle size diameter of about 45-65 μm, about 45-55 μm, about 50-55 μm, or about 50 μm, wherein the first microcrystalline cellulose portion comprises about 45 to about 90%, e.g., about 50 to about 90%, of the total weight of the formulation, and the second microcrystalline portion comprises about 10% of the total weight of the formulation; and c) tribasic calcium phosphate comprising about 0.5-1.0%, e.g., about 0.8%, of the total weight of the formulation.

In a specific embodiment of such a method, the powder formulation comprises DHE mesylate. In another specific embodiment of such a method, the powder formulation is administered to a single nostril of the human having a headache, e.g., migraine. In yet another specific embodiment of such a method, a portion of the powder formulation is administered to each nostril of the human having a headache, e.g. headache. For example, in a specific embodiment, about half of the powder formulation is administered to one nostril and about half of the powder formulation is administered to the other nostril of the human having a headache, e.g. headache.

In instances wherein such a method is a method of treating migraine, the method can be a method of acute treatment of migraine with or without aura.

In yet another particular embodiment of such a method of treating headache, including migraine, the powder formulation further comprises caffeine, for example, about 1-25% caffeine, e.g., anhydrous caffeine.

In specific embodiments of such a method of treating headache, including migraine, the total amount of the powder formulation administered is 5, 10, 15, 20, 25, 30, 35, 40, 45, or 50 mg. In certain embodiments, the total amount of the powder formulation is administered into a single nostril. In other embodiments, a portion of the total amount of the powder formulation is administered into each nostril. In yet other embodiments, about half of the total amount of the powder formulation is administered into one nostril and the remaining half is administered into the other nostril.

In a particular embodiment of such a method of treating headache, including migraine utilizing a powder formulation comprising about 0.1-2.0 mg DHE, the powder formulation is administered such that the mean $T_{max}$ of DHE is about 10-50 minutes. In another embodiment, the powder formulation is administered such that the mean $T_{max}$ of DHE is about 2-50 minutes. In another embodiment, the powder formulation is administered such that the mean $T_{max}$ of DHE is about 2-30 minutes. In another particular embodiment, the powder formulation is administered such that the mean $C_{max}$ of DHE is about 0.5-40 ng/mL. In yet another particular embodiment, the powder formulation is administered such that the mean $AUC_{0-inf}$ of DHE is about 1-200 ng·h/mL. In another specific embodiment of such a method of treating headache, including migraine, the powder formulation is administered such that the mean $T_{1/2}$ of DHE is about 100-300 minutes. In still another embodiment of such a method of treating headache, including migraine, the intersubject variability in DHE $C_{max}$ is less than 30%.

In another particular aspect, presented herein is a method of treating headache, including migraine, comprising: intranasally administering to a human having a headache, e.g., migraine, a powder formulation comprising: a) DHE, or a pharmaceutically acceptable salt thereof, e.g., DHE mesylate, wherein the total dose of DHE administered is about 0.1 mg; b) a microcrystalline cellulose component comprising a first microcrystalline cellulose portion with a mean particle size of about 30 μm or less, for example, about 15-30 μm, about 18-20 μm, or about 20 μm, and a second microcrystalline cellulose portion with a mean particle size diameter of about 45-65 μm, for example, about 45-55 μm or about 50-55 μm, e.g., about 50 μm, wherein the first microcrystalline cellulose portion comprises about 80 to about 90%, e.g., about 85 to about 90%, of the total weight of the formulation, and the second microcrystalline portion comprises about 10% of the total weight of the formulation; and c) tribasic calcium phosphate comprising about 0.5-1.0%, e.g., about 0.8%, of the total weight of the formulation. In yet another particular embodiment of such a method of treating headache, including migraine, the powder formulation further comprises caffeine, for example, about 1-2% caffeine, e.g. anhydrous caffeine.

In another specific embodiment of such a method, the powder formulation is administered to a single nostril of the human having a migraine. In yet another specific embodiment of such a method, a portion of the powder formulation is administered to each nostril of the human having a headache, e.g., migraine. For example, in a specific embodiment, about half of the powder formulation is administered to one nostril and about half of the powder formulation is administered to the other nostril of the human having a headache, e.g., migraine. In specific embodiments of such a method of treating headache, including migraine, the total amount of the powder formulation administered is about 5, 10, 15, 20, 25, 30, 35, 40, 45, or 50 mg, into a single or into both nostrils.

In instances wherein such a method is a method of treating migraine, the method can be acute treatment of migraine with or without aura.

In a particular embodiment of such a method of treating headache, including migraine, utilizing a powder formulation comprising about 0.1 mg DHE, the powder formulation is administered such that the mean $T_{max}$ of DHE is about 10-30 minutes. In another embodiment, the powder formulation is administered such that the mean $T_{max}$ of DHE is about 2-50 minutes. In another embodiment, the powder formulation is administered such that the mean $T_{max}$ of DHE is about 2-30 minutes. In another particular embodiment of such a method of treating headache, including migraine, the powder formulation is administered such that the mean $C_{max}$ of DHE is about 0.1-6 ng/mL. In another embodiment of such a method of treating headache, including migraine, the powder formulation is administered such that the mean $AUC_{0-inf}$ of DHE is about 1-15 ng·h/mL. In another embodiment of such a method of treating headache, including migraine, the powder formulation is administered such that the mean $T_{1/2}$ of DHE is about 100-300 minutes. In yet another particular embodiment of such a method of treating headache, including migraine, the powder formulation is administered such that the mean $T_{max}$ of DHE is about 2-30 minutes, the mean $C_{max}$ of DHE is about 0.1-6 ng/mL, the mean $AUC_{0-inf}$ of DHE is about 1-15 ng·h/mL, and the mean $T_{1/2}$ of DHE is about 100-300 minutes. In still another embodiment of such a method of treating headache, including migraine, the intersubject variability in DHE $C_{max}$ is less than 30%.

In yet another aspect, presented herein is a method of treating headache, including migraine, comprising: intranasally administering to a human having a headache, e.g, migraine, a powder formulation comprising: a) DHE, or a pharmaceutically acceptable salt thereof, e.g., DHE mesylate, wherein the total dose of DHE being administered is about 0.5 mg; b) a microcrystalline cellulose component comprising a first microcrystalline cellulose portion with a mean particle size of about 30 μm or less, for example, about 15-30 μm, about 18-20 μm, or about 20 μm, and a second microcrystalline cellulose portion with a mean particle size diameter of about 45-65 μm, for example, about 45-55 μm or about 50-55 μm, e.g., about 50 μm, wherein the first microcrystalline cellulose portion comprises about 75 to about 90%, e.g., about 80 to about 90%, of the total weight of the formulation, and the second microcrystalline portion comprises about 10% of the total weight of the formulation; and c) tribasic calcium phosphate comprising about 0.5-1.0%, e.g., about 0.8%, of the total weight of the formulation. In yet another particular embodiment of such a method of treating headache, including migraine, the powder formulation further comprises caffeine, for example, about 5-10% caffeine, e.g. anhydrous caffeine.

In another specific embodiment of such a method, the powder formulation is administered to a single nostril of the human having a headache, e.g., migraine. In yet another specific embodiment of such a method, a portion of the powder formulation is administered to each nostril of the human having a headache, e.g., migraine. For example, in a specific embodiment, about half of the powder formulation is administered to one nostril and about half of the powder formulation is administered to the other nostril of the human having a headache, e.g., migraine. In specific embodiments of such a method of treating headache, including migraine, the total amount of the powder formulation administered is about 5, 10, 15, 20, 25, 30, 35, 40, 45, or 50 mg, into a single or into both nostrils.

In a specific embodiment of such a method, the method is a method for the acute treatment of migraine with or without aura.

In a particular embodiment of such a method of treating headache, including migraine, comprises utilizing a powder formulation comprising about 0.5 mg DHE, the powder formulation is administered such that the mean $T_{max}$ of DHE is about 10-50 minutes. In another embodiment, the powder formulation is administered such that the mean $T_{max}$ of DHE is about 2-50 minutes. In another embodiment, the powder formulation is administered such that the mean $T_{max}$ of DHE is about 2-30 minutes. In another particular embodiment of such a method of treating headache, including migraine, the powder formulation is administered such that the mean $C_{max}$ of DHE is about 1.0-15 ng/mL. In another embodiment of such a method of treating headache, including migraine, the powder formulation is administered such that the mean $AUC_{0-inf}$ of DHE is about 10-50 ng·h/mL. In another embodiment of such a method of treating headache, including migraine, the powder formulation is administered such that the mean $T_{1/2}$ of DHE is about 100-300 minutes. In yet another particular embodiment of such a method of treating headache, including migraine, the powder formulation is administered such that the mean $T_{max}$ of DHE is about 2-50 minutes, the mean $C_{max}$ of DHE is about 1.0-15 ng/mL, the mean $AUC_{0-inf}$ of DHE is about 10-50 ng·h/mL, and the mean $T_{1/2}$ of DHE is about 100-300 minutes. In still another embodiment of such a method of treating headache, including migraine, the intersubject variability in DHE $C_{max}$ is less than 30%.

In yet another aspect, presented herein is a method of treating headache, including migraine, comprising: intranasally administering to a human having a headache, e.g., migraine a powder formulation comprising: a) DHE, or a pharmaceutically acceptable salt thereof, e.g., DHE mesylate, wherein the total dose of DHE being administered is about 1.0 mg; b) a microcrystalline cellulose component comprising a first microcrystalline cellulose portion with a mean particle size of about 30 μm or less, for example, about 15-30 μm, about 18-20 μm, or about 20 μm, and a second microcrystalline cellulose portion with a mean particle size diameter of about 45-65 μm, for example, about 45-55 μm or about 50-55 μm, e.g., about 50 μm, wherein the first microcrystalline cellulose portion comprises about 65 to about 90%, e.g., about 70 to about 90%, of the total weight of the formulation, and the second microcrystalline portion comprises about 10% of the total weight of the formulation; and c) tribasic calcium phosphate comprising about 0.5-1.0%, e.g., about 0.8%, of the total weight of the formulation. In yet another particular embodiment of such a method of treating migraine, the powder formulation further comprises caffeine, for example, about 10-15% caffeine, e.g. anhydrous caffeine.

In another specific embodiment of such a method, the powder formulation is administered to a single nostril of the human having a headache, e.g., migraine. In yet another specific embodiment of such a method, a portion of the powder formulation is administered to each nostril of the human having a headache, e.g., migraine. For example, in a specific embodiment, about half of the powder formulation is administered to one nostril and about half of the powder formulation is administered to the other nostril of the human having a migraine. In specific embodiments of such a method of treating headache, including migraine, the total amount of the powder formulation administered is about 5, 10, 15, 20, 25, 30, 35, 40, 45, or 50 mg, into a single or into both nostrils.

In a specific embodiment of such a method, the method is a method for the acute treatment of migraine with or without aura.

In a particular embodiment of such a method of treating headache, including migraine, utilizing a powder formulation comprising about 1.0 mg DHE, the powder formulation is administered such that the mean $T_{max}$ of DHE is about 10-50 minutes. In another embodiment, the powder formulation is administered such that the mean $T_{max}$ of DHE is about 2-50 minutes. In another embodiment, the powder formulation is administered such that the mean $T_{max}$ of DHE is about 2-30 minutes. In another particular embodiment of such a method of treating headache, including migraine, the powder formulation is administered such that the mean $C_{max}$ of DHE is about 2.0-20 ng/mL. In another embodiment of such a method of treating headache, including migraine, the powder formulation is administered such that the mean $AUC_{0-inf}$ of DHE is about 15-110 ng·h/mL. In another embodiment of such a method of treating headache, including migraine, the powder formulation is administered such that the mean $T_{1/2}$ of DHE is about 100-300 minutes. In yet another particular embodiment of such a method of treating headache, including migraine, the powder formulation is administered such that the mean $T_{max}$ of DHE is about 2-50 minutes, the mean $C_{max}$ of DHE is about 2.0-20 ng/mL, the mean $AUC_{0-inf}$ of DHE is about 15-110 ng·h/mL, and the mean $T_{1/2}$ of DHE is about 100-300 minutes. In still another embodiment of such a method of treating migraine, the intersubject variability in DHE $C_{max}$ is less than 30%.

In yet another aspect, presented herein is a method of treating headache, including migraine, comprising: intranasally administering to a human having a migraine a powder formulation comprising: a) DHE, or a pharmaceutically acceptable salt thereof, e.g., DHE mesylate, wherein the total dose of DHE is about 2.0 mg; b) a microcrystalline cellulose component comprising a first microcrystalline cellulose portion with a mean particle size of about 30 μm or less, for example, about 15-30 μm, about 18-20 μm, or about 20 μm, and a second microcrystalline cellulose portion with a mean particle size diameter of about 45-65 μm, for example, about 45-55 lam or about 50-55 μm, e.g., about 50 μm, wherein the first microcrystalline cellulose portion comprises about 45 to about 80%, e.g., about 50 to about 80%, of the total weight of the formulation, and the second microcrystalline portion comprises about 10% of the total weight of the formulation; and c) tribasic calcium phosphate comprising about 0.5-1.0%, e.g., about 0.8%, of the total weight of the formulation. In yet another particular embodiment of such a method of treating headache, including migraine, the powder formulation further comprises caffeine, for example, about 20-30% caffeine, e.g. anhydrous caffeine.

In another specific embodiment of such a method, the powder formulation is administered to a single nostril of the human having a headache, e.g., migraine. In yet another specific embodiment of such a method, a portion of the powder formulation is administered to each nostril of the human having a headache, e.g., migraine. For example, in a specific embodiment, about half of the powder formulation is administered to one nostril and about half of the powder formulation is administered to the other nostril of the human having a headache, e.g, migraine. In specific embodiments of such a method of treating headache, including migraine, the total amount of the powder formulation administered is about 5, 10, 15, 20, 25, 30, 35, 40, 45, or 50 mg, into a single or into both nostrils.

In a specific embodiment of such a method, the method is a method for the acute treatment of migraine with or without aura.

In a particular embodiment of such a method of treating headache, including migraine, utilizing a powder formulation comprising about 2.0 mg DHE, the powder formulation is administered such that the mean $T_{max}$ of DHE is about 10-50 minutes. In another embodiment, the powder formulation is administered such that the mean $T_{max}$ of DHE is about 2-50 minutes. In another embodiment, the powder formulation is administered such that the mean $T_{max}$ of DHE is about 2-30 minutes. In another particular embodiment of such a method of treating headache, including migraine, the powder formulation is administered such that the mean $C_{max}$ of DHE is about 2.0-50 ng/mL. In another embodiment of such a method of treating headache, including migraine, the powder formulation is administered such that the mean $AUC_{0-inf}$ of DHE is about 15-200 ng·h/mL. In another embodiment of such a method of treating headache, including migraine, the powder formulation is administered such that the mean $T_{1/2}$ of DHE is about 100-300 minutes. In yet another particular embodiment of such a method of treating headache, including migraine, the powder formulation is administered such that the mean $T_{max}$ of DHE is about 2-50 minutes, the mean $C_{max}$ of DHE is about 2.0-50 ng/mL, the mean $AUC_{0-inf}$ of DHE is about 15-200 ng·h/mL, and the mean $T_{1/2}$ of DHE is about 100-300 minutes. In still another embodiment of such a method of treating headache, including migraine, the intersubject variability in DHE $C_{max}$ is less than 30%.

In one aspect, presented herein is a method of treating headache, including migraine, comprising: intranasally administering to a human having a headache a powder formulation comprising: a) DHE, or a pharmaceutically acceptable salt thereof, wherein the total dose of DHE being administered is about 0.1-10.0 mg; b) a microcrystalline cellulose component comprising a first microcrystalline cellulose portion with a mean particle size diameter of about 30 lam or less, for example, about 15-30 μm, about 18-20 μm, or about 20 μm, and a second microcrystalline cellulose portion with a mean particle size diameter of about 45-65 μm, for example, about 45-55 μm or about 50-55 μm, e.g., about 50 μm, wherein the first microcrystalline cellulose portion comprises about 3 to about 90%, e.g., about 8 to about 90%, of the total weight of the powder formulation of the total weight of the formulation, and the second microcrystalline portion comprises about 10% of the total weight of the formulation.

In a particular embodiment of such a method of treating headache, including treating migraine, the powder formulation comprises DHE mesylate. In certain embodiments of such a method, the powder formulation is administered to a single nostril of the human having a headache, including migraine. In other embodiments of such a method, a portion of the powder formulation is administered to each nostril of the human having a headache, e.g., migraine. For example, in a specific embodiment of such a method, about half of the powder formulation is administered to one nostril and about half of the powder formulation is administered to the other nostril of the human having a headache, e.g., migraine.

In particular embodiments of such methods of treating headache, including migraine, the total dose of DHE administered is about 0.1-5.0 mg. In certain other embodiments, the total dose of DHE administered is about 0.5-5.0 mg. In certain other embodiments, the total dose of DHE administered is about 0.5-3.0 mg. In certain other embodiments, the total dose of DHE administered is about 1.0-2.0 mg. In particular embodiments of such methods, the total dose of DHE administered is about 0.1 mg, about 0.5 mg, about 1.0 mg, about 1.5 mg, about 2.0 mg, about 3.0 mg, about 4.0 mg, about 5.0 mg, about 7.5 mg, or about 10.0 mg. In certain embodiments, the total dose is administered into a single nostril. In other embodiments, a portion of the total dose is administered into each nostril. In yet other embodiments, about half of the total dose is administered into one nostril and the remaining half is administered into the other nostril.

In specific embodiments of such a method of treating headache, including migraine, the total amount of the powder formulation administered is 5, 10, 15, 20, 25, 30, 35, 40, 45, or 50 mg. In certain embodiments, the total amount of the powder formulation is administered into a single nostril. In other embodiments, a portion of the total amount of the powder formulation is administered into each nostril. In yet other embodiments, about half of the total amount of the powder formulation is administered into one nostril and the remaining half is administered into the other nostril.

In certain embodiments of such methods of treating headache, including migraine, the powder formulation further comprises a fluidizing agent. Fluidizing agents include but are not limited to tribasic calcium phosphate, talc, silicon dioxide, and magnesium stearate. In some embodiments, the fluidizing agent is tribasic calcium phosphate. In certain embodiments, the tribasic calcium phosphate comprises about 0.5-1.0% of the total weight of the formulation. In specific embodiments of the methods of treating migraine, the tribasic calcium phosphate comprises about 0.8% of the total weight of the formulation.

In certain other embodiments, the powder formulations utilized as part of such methods of treating headache, including migraine, further comprise caffeine, for example, anhydrous caffeine In specific embodiments, the powder formulations utilized as part of the methods of treating migraine comprise about 1-60% caffeine, for example, anhydrous caffeine.

In particular embodiments, such methods are methods for the acute treatment of migraine with or without aura.

In certain embodiments, such methods of treating headache, including migraine, comprise administering the powder formulation such that the mean $T_{max}$ of DHE is about 10-50 minutes. In another embodiment, the powder formulation is administered such that the mean $T_{max}$ of DHE is about 2-50 minutes. In another embodiment, the powder formulation is administered such that the mean $T_{max}$ of DHE is about 2-30 minutes. In other embodiments, such methods of treating headache, e.g., migraine, comprise administering the powder formulation such that the mean $C_{max}$ of DHE is about 0.5-100 ng/mL. In yet other embodiments, the methods of treating headache, including migraine, comprise administering the powder formulation such that the mean $AUC_{0\text{-}inf}$ of DHE is about 4-500 ng·h/mL. In yet other embodiments, the methods of treating headache, including migraine, comprise administering the powder formulation such that the mean $T_{1/2}$ of DHE is about 110-260 minutes. In yet other embodiments, the methods of treating headache, including migraine, comprise administering the intersubject variability in DHE $C_{max}$ is less than 30%.

In yet another aspect, presented herein are methods for treating headache, including migraine, comprising intranasally administering to a human having a headache, e.g., a migraine, a powder formulation comprising: a) DHE, or a pharmaceutically acceptable salt thereof, e.g., DHE mesylate; b) a microcrystalline cellulose component comprising a first microcrystalline cellulose portion having a mean particle diameter size of less than about 30 µm (e.g., about 15-30 µm, about 15-20 µm, about 18-20 µm, or about 20 µm), and a second microcrystalline cellulose portion having a mean particle diameter size of about 45-65 µm (e.g., about 45-55 µm, about 50-55 µm, or about 50 µm); c) tribasic calcium phosphate; and, optionally d) caffeine, for example anhydrous caffeine, wherein the powder formulation contains the parameters of any of the representative DHE powder formulations presented, below, in Table 1.

TABLE 1

| | w/w % of total powder formulation | | | |
|---|---|---|---|---|
| DHE Dose (mg) | $1^{st}$ MCC portion | $2^{nd}$ MCC portion | TCP | Caffeine |
| 0.1-10 | 38-94 | 5-15 | 0.5-1.5 | 0 |
| 0.1-2 | 75-94 | 5-15 | 0.5-1.5 | 0 |
| 1-5 | 60-90 | 5-15 | 0.5-1.5 | 0 |
| 1-2 | 74-90 | 5-15 | 0.5-1.5 | 0 |
| 0.1 | 73-94 | 5-15 | 0.5-1.5 | 0 |
| 0.5 | 76-92 | 5-15 | 0.5-1.5 | 0 |
| 1.0 | 74-90 | 5-15 | 0.5-1.5 | 0 |
| 2.0 | 69-85 | 5-15 | 0.5-1.5 | 0 |
| 5.0 | 55-71 | 5-15 | 0.5-1.5 | 0 |
| 8.0 | 41-57 | 5-15 | 0.5-1.5 | 0 |
| 10.0 | 32-48 | 5-15 | 0.5-1.5 | 0 |

TABLE 1-continued

| | w/w % of total powder formulation | | | |
|---|---|---|---|---|
| DHE Dose (mg) | $1^{st}$ MCC portion | $2^{nd}$ MCC portion | TCP | Caffeine |
| 0.1-10 | 4-89 | 5-15 | 0.5-1.5 | 1-58 |
| 0.1-2 | 57-88 | 5-15 | 0.5-1.5 | 1-23 |
| 1-5 | 8-57 | 5-15 | 0.5-1.5 | 12-58 |
| 1-2 | 57-73 | 5-15 | 0.5-1.5 | 12-23 |
| 0.1 | 76-93.5 | 5-15 | 0.5-1.5 | 0.5-2 |
| 0.5 | 66-89.5 | 5-15 | 0.5-1.5 | 2.5-10 |
| 1.0 | 54-85 | 5-15 | 0.5-1.5 | 5-20 |
| 2.0 | 29-75 | 5-15 | 0.5-1.5 | 10-40 |
| 5.0 | 1-46 | 5-15 | 0.5-1.5 | 25-59 |
| 8.0 | 0.3-32 | 5-15 | 0.5-1.5 | 25-56 |
| 10.0 | 0.1-12 | 5-15 | 0.5-1.5 | 25-47 |
| 0.1-10 | 38-94 | 10 | 0.5-1.5 | 0 |
| 0.1-2 | 75-94 | 10 | 0.5-1.5 | 0 |
| 1-5 | 60-90 | 10 | 0.5-1.5 | 0 |
| 1-2 | 74-90 | 10 | 0.5-1.5 | 0 |
| 0.1 | 73-94 | 10 | 0.5-1.5 | 0 |
| 0.5 | 76-92 | 10 | 0.5-1.5 | 0 |
| 1.0 | 74-90 | 10 | 0.5-1.5 | 0 |
| 2.0 | 69-85 | 10 | 0.5-1.5 | 0 |
| 5.0 | 55-71 | 10 | 0.5-1.5 | 0 |
| 8.0 | 41-57 | 10 | 0.5-1.5 | 0 |
| 10.0 | 32-48 | 10 | 0.5-1.5 | 0 |
| 0.1-10 | 4-89 | 10 | 0.5-1.5 | 1-58 |
| 0.1-2 | 57-88 | 10 | 0.5-1.5 | 1-23 |
| 1-5 | 8-57 | 10 | 0.5-1.5 | 12-58 |
| 1-2 | 57-73 | 10 | 0.5-1.5 | 12-23 |
| 0.1 | 76-93.5 | 10 | 0.5-1.5 | 0.5-2 |
| 0.5 | 66-89.5 | 10 | 0.5-1.5 | 2.5-10 |
| 1.0 | 54-85 | 10 | 0.5-1.5 | 5-20 |
| 2.0 | 29-75 | 10 | 0.5-1.5 | 10-40 |
| 5.0 | 1-46 | 10 | 0.5-1.5 | 25-59 |
| 8.0 | 0.3-32 | 10 | 0.5-1.5 | 25-56 |
| 10.0 | 0.1-12 | 10 | 0.5-1.5 | 25-47 |
| 0.1-10 | 38-94 | 5-15 | 0.8 | 0 |
| 0.1-2 | 75-94 | 5-15 | 0.8 | 0 |
| 1-5 | 60-90 | 5-15 | 0.8 | 0 |
| 1-2 | 74-90 | 5-15 | 0.8. | 0 |
| 0.1 | 73-94 | 5-15 | 0.8 | 0 |
| 0.5 | 76-92 | 5-15 | 0.8 | 0 |
| 1.0 | 74-90 | 5-15 | 0.8 | 0 |
| 2.0 | 69-85 | 5-15 | 0.8 | 0 |
| 5.0 | 55-71 | 5-15 | 0.8 | 0 |
| 8.0 | 41-57 | 5-15 | 0.8 | 0 |
| 10.0 | 32-48 | 5-15 | 0.8 | 0 |
| 0.1-10 | 4-89 | 5-15 | 0.8 | 1-58 |
| 0.1-2 | 57-88 | 5-15 | 0.8 | 1-23 |
| 1-5 | 8-57 | 5-15 | 0.8 | 12-58 |
| 1-2 | 57-73 | 5-15 | 0.8 | 12-23 |
| 0.1 | 76-93.5 | 5-15 | 0.8 | 0.5-2 |
| 0.5 | 66-89.5 | 5-15 | 0.8 | 2.5-10 |
| 1.0 | 54-85 | 5-15 | 0.8 | 5-20 |
| 2.0 | 29-75 | 5-15 | 0.8 | 10-40 |
| 5.0 | 1-46 | 5-15 | 0.8 | 25-59 |
| 8.0 | 0.3-32 | 5-15 | 0.8 | 25-56 |
| 10.0 | 0.1-12 | 5-15 | 0.8 | 25-47 |
| 0.1-10 | 38-94 | 10 | 0.8 | 0 |
| 0.1-2 | 75-94 | 10 | 0.8 | 0 |
| 1-5 | 60-90 | 10 | 0.8 | 0 |
| 1-2 | 74-90 | 10 | 0.8 | 0 |
| 0.1 | 73-94 | 10 | 0.8 | 0 |
| 0.5 | 76-92 | 10 | 0.8 | 0 |
| 1.0 | 74-90 | 10 | 0.8 | 0 |
| 2.0 | 69-85 | 10 | 0.8 | 0 |
| 5.0 | 55-71 | 10 | 0.8 | 0 |
| 8.0 | 41-57 | 10 | 0.8 | 0 |
| 10.0 | 32-48 | 10 | 0.8 | 0 |
| 0.1-10 | 4-89 | 10 | 0.8 | 1-58 |
| 0.1-2 | 57-88 | 10 | 0.8 | 1-23 |
| 1-5 | 8-57 | 10 | 0.8 | 12-58 |
| 1-2 | 57-73 | 10 | 0.8 | 12-23 |

TABLE 1-continued

| | w/w % of total powder formulation | | | |
|---|---|---|---|---|
| DHE Dose (mg) | 1st MCC portion | 2nd MCC portion | TCP | Caffeine |
| 0.1 | 76-93.5 | 10 | 0.8 | 0.5-2 |
| 0.5 | 66-89.5 | 10 | 0.8 | 2.5-10 |
| 1.0 | 54-85 | 10 | 0.8 | 5-20 |
| 2.0 | 29-75 | 10 | 0.8 | 10-40 |
| 5.0 | 1-46 | 10 | 0.8 | 25-59 |
| 8.0 | 0.3-32 | 10 | 0.8 | 25-56 |
| 10.0 | 0.1-12 | 10 | 0.8 | 25-47 |

MCC = microcrystalline cellulose
TCP = tribasic calcium phosphate

6. EXAMPLES

6.1 Example 1: Preparation of DHE Powder Formulations

6.1.1 Preparation of 0.1 Mg DHE Powder Formulation

Powder formulations comprising 0.1 mg DHE were prepared as described herein.

Materials. Dihydroergotamine mesylate (99.7% purity; primary particle distribution: Dv10: 5.3 μm; Dv50: 17.7 μm; Dv90: 69.3 μm; "DvX" refers to the maximum particle diameter below which X % of the sample exists; for example, "Dv10" refers to the maximum particle diameter below which 10% of the sample exists); microcrystalline cellulose, Ceolus®PH-F20JP (nominal particle size: 20 μm, less than 1% retained when sieved through mesh size 400; Asahi Kasei Chemicals Corporation); Microcrystalline cellulose, Ceolus®PH-301 (nominal particle size: 50 μm, less than 1% retained when sieved through mesh size 60 and less than 30% retained when sieved through mesh size 200; Asahi Kasei Chemicals Corporation); Tribasic calcium phosphate ($Cas(OH)(PO_4)_3$; Mallinckrodt Chemicals); HPMC capsule, size 2, Quali-V (Qualicaps Co., Ltd).

Procedure. Two hundred-fifty mg Ceolus®PH-301 and 1110 mg Ceolus®PH-F20JP were combined in a glass vial and mixed with vigorous shaking for approximately 10 minutes. Twenty mg tribasic calcium phosphate was then added and mixed with vigorous shaking for approximately 10 minutes. Ten mg dihydroergotamine mesylate was then added and mixed with vigorous shaking for approximately 10 minutes. An additional 1110 mg Ceolus®PH-F20JP was then added and mixed with vigorous shaking for approximately 10 minutes. The resulting DHE powder formulation was encapsulated into the HPMC capsules (25 mg/capsule±1 mg) and the length of each capsule was adjusted to 17.8±0.4 mm using a capsule sizer.

6.1.2 Preparation of 0.5 Mg DHE Powder Formulation

Powder formulations comprising 0.5 mg DHE were prepared as described herein.

Materials. Dihydroergotamine mesylate (99.7% purity; primary particle distribution: Dv10: 5.3 μm; Dv50: 17.7 μm; Dv90: 69.3 μm); microcrystalline cellulose, Ceolus® PH-F20JP (nominal particle size: 20 μm, less than 1% retained when sieved through mesh size 400; Asahi Kasei Chemicals Corporation); Microcrystalline cellulose, Ceolus®PH-301 (nominal particle size: 50 μm, less than 1% retained when sieved through mesh size 60 and less than 30% retained when sieved through mesh size 200; Asahi Kasei Chemicals Corporation); Tribasic calcium phosphate ($Cas(OH)(PO_4)_3$; Mallinckrodt Chemicals); HPMC capsule, size 2, Quali-V (Qualicaps Co., Ltd).

Procedure. Sixty mg Ceolus®PH-301 and 261.6 mg Ceolus®PH-F20JP were combined in a glass vial and mixed with vigorous shaking for approximately 10 minutes. 4.8 mg tribasic calcium phosphate was then added and mixed with vigorous shaking for approximately 10 minutes. Twelve mg dihydroergotamine mesylate was then added and mixed with vigorous shaking for approximately 10 minutes. An additional 261.6 mg Ceolus®PH-F20JP was then added and mixed with vigorous shaking for approximately 10 minutes. The resulting DHE powder formulation was encapsulated into the HPMC capsules (25 mg/capsule±1 mg) and the length of each capsule was adjusted to 17.8±0.4 mm using a capsule sizer. Similar procedures were also utilized to yield capsules with 1.5 mg±0.5 mg of such a 0.5 mg DHE powder formulation per capsule.

6.1.3 Preparation of 1.0 Mg DHE Powder Formulation

Powder formulations comprising 1.0 mg DHE were prepared as described herein.

Materials. Dihydroergotamine mesylate (99.7% purity; primary particle distribution: Dv10: 5.3 μm; Dv50: 17.7 μm; Dv90: 69.3 μm); microcrystalline cellulose, Ceolus®PH-F20JP (nominal particle size: 20 μm, less than 1% retained when sieved through mesh size 400; Asahi Kasei Chemicals Corporation); Microcrystalline cellulose, Ceolus®PH-301 (nominal particle size: 50 μm, less than 1% retained when sieved through mesh size 60 and less than 30% retained when sieved through mesh size 200; Asahi Kasei Chemicals Corporation); Tribasic calcium phosphate ($Cas(OH)(PO_4)_3$; Mallinckrodt Chemicals); HPMC capsule, size 2, Quali-V (Qualicaps Co., Ltd).

Procedure. Sixty mg Ceolus®PH-301 and 255.6 mg Ceolus®PH-F20JP were combined in a glass vial and mixed with vigorous shaking for approximately 10 minutes. 4.8 mg tribasic calcium phosphate was then added and mixed with vigorous shaking for approximately 10 minutes. Twenty-four mg dihydroergotamine mesylate was then added and mixed with vigorous shaking for approximately 10 minutes. An additional 255.6 mg Ceolus®PH-F20JP was then added and mixed with vigorous shaking for approximately 10 minutes. The resulting DHE powder formulation was encapsulated into the HPMC capsules (25 mg/capsule±1 mg) and the length of each capsule was adjusted to 17.8±0.4 mm using a capsule sizer.

6.1.4 DHE Powder Formulations

Presented below, in Table 2, are representative DHE powder formulations that can be utilized in the methods of treating headache, including migraine, presented herein. Such formulations can be produced, for example, following procedures as described in the preceding examples. The total amount of such formulations can be administered intranasally into a single nostril, or, alternatively, a portion can be administered into each nostril; for example, about one-half of the total can be administered into each nostril.

TABLE 2

| Components | 0.1 mg DHE dose | 0.5 mg DHE dose | 1.0 mg DHE dose mg | 2.0 mg DHE dose | 5.0 mg DHE dose |
|---|---|---|---|---|---|
| DHE mesylate | 0.116 | 0.58 | 1.16 | 2.32 | 5.80 |
| MCC (Ceolus PH-F20JP) | 22.184 | 21.72 | 21.14 | 19.98 | 16.50 |
| MCC (Ceolus PH-301 | 2.50 | 2.50 | 2.50 | 2.50 | 2.50 |
| Tribasic calcium phosphate | 0.20 | 0.20 | 0.20 | 0.20 | 0.20 |
| Total unit dose wt | 25 | 25 | 25 | 25 | 25 |

Units: mg

DHE-dihydroergotamine mesylate

MCC (Ceolus PH-F20JP)-Microcrystalline cellulose nominal particle size 20 μm; less than 1% retained when sieved through mesh size 400.

MCC (Ceolus PH 301)-Microcrystalline cellulose nominal particle size 50 μm; less than 1% retained when sieved through mesh size 60 and less than 30% retained when sieved through mesh size 200.

6.1.5 DHE Powder Formulations Comprising Caffeine

Presented below, in Table 3, are representative DHE powder formulations comprising caffeine that can be utilized in the methods of treating headache, including migraine, presented herein. Such caffeine-containing formulations can be produced, for example, following procedures similar to those described in the preceding examples. The total amount of such formulations can be administered intranasally into a single nostril, or, alternatively, a portion can be administered into each nostril; for example, about one-half of the total can be administered into each nostril.

TABLE 3

| Components | 0.1 mg DHE dose | 0.5 mg DHE dose | 0.5 mg DHE dose | 1.0 mg DHE dose | 1.0 mg DHE dose | 2.0 mg DHE dose | 5.0 mg DHE dose |
|---|---|---|---|---|---|---|---|
| DHE mesylate | 0.116 | 0.58 | 0.58 | 1.16 | 1.16 | 2.32 | 5.80 |
| Caffeine anhydrous | 0.29 | 1.45 | 1.25 | 2.9 | 2.5 | 5.8 | 14.5 |
| MCC (Ceolus PH-F20JP) | 21.894 | 20.27 | 20.47 | 18.24 | 18.64 | 14.18 | 2.00 |
| MCC (Ceolus PH-301 | 2.50 | 2.50 | 2.50 | 2.50 | 2.50 | 2.50 | 2.50 |
| Tribasic calcium phosphate | 0.20 | 0.20 | 0.20 | 0.20 | 0.20 | 0.20 | 0.20 |
| Total unit dose wt | 25 | 25 | 25 | 25 | 25 | 25 | 25 |

Units: mgs

DHE-dihydroergotamine mesylate

MCC (Ceolus PH-F20JP)-Microcrystalline cellulose nominal particle size 20 um; less than 1% retained when sieved through mesh size 400.

MCC (Ceolus PH 301)-Microcrystalline cellulose nominal particle size 50 um; less than 1% retained when sieved through mesh size 60 and less than 30% retained when sieved through mesh size 200

6.2 Example 2: Pharmacokinetic Study of Intranasal Dihydroergotamine Formulations in Primates The study described herein is designed to assess the pharmacokinetics of plasma dihydroergotamine (DHE) and 8'-hydroxy DHE levels after intranasal administration using DHE powder formulations described herein, and to compare the pharmacokinetic profiles achieved via intranasal administration of such formulations with those of comparative DHE formulations administered via various dosing routes.

The study utilizes Cynomolgus monkeys (*Macaca fascicularis*, purpose bred) because the nasal cavity of such monkeys is morphologically similar to that in humans, and is commonly used as an experimental animal.

Methods.

Animals. Six male Cynomolgus monkeys (*Macaca fascicularis*, purpose bred), 4 to 6 years old are used, following accredited animal welfare standards.

Test Powder Formulations. Powder formulations containing 0.1 mg DHE, 0.5 mg DHE and 1.0 mg DHE, as described in the Examples, above, and summarized in Table 3, above, are tested. With respect to the 0.5 mg DHE formulation, a 25 mg single nostril dose is tested, as is a 12.5 mg two-nostril dose (total dose=25 mg). Powder formulations containing 0.5 mg DHE containing 1.25 mg anhydrous caffeine and 1.0 mg DHE containing 2.5 mg anhydrous caffeine, as summarized in Table xxx, above, are also tested. With respect to each of the 0.5 mg DHE formulations, a 25 mg single nostril dose is tested, as is a 12.5 mg two-nostril dose (total dose=25 mg). The powder formulations are encapsulated as described in the Examples above, and are administered using a Fit-lizer™ intranasal dispenser (SNBL, LTD).

Comparative Formulations: The following formulations and routes of administration are tested for comparison purposes: IM DHE solution: 0.1 mg DHE mesylate of solution of D.H.E. 45®(Valeant Pharmaceuticals North America) for intramuscular (IM) administration; IV DHE solution: 0.1 mL of D.H.E. 45®(Valeant Pharmaceuticals North America) containing 0.1 mg DHE mesylate diluted with water for injection to 1.0 mL; 0.5 mg IN DHE solution: 0.5 mg DHE mesylate nasal spray (Migranal®; Valeant Pharmaceuticals North America); 1.0 mg IN DHE solution: 1.0 mg DHE mesylate nasal spray (Migranal®; Valeant Pharmaceuticals North America); and 0.1 mg IN DHE solution: 0.1 mg DHE mesylate (Migranal® diluted to 0.1 mg concentration with saline).

Dosing. The dose levels of the DHE powder formulations are set at levels equivalent to clinical doses of 0.1, 0.5, and 1.0 mg/body. As comparisons, the doses of the comparative formulations include ones set at the same levels as clinical doses of 1.0 mg/body for injection (IV and IM) and 0.5 mg/nostril for intranasal administration.

Powder DHE formulations are administered intranasally using a Fit-liter® dispenser as noted above, and administration is confirmed by use of a breath monitoring device while holding the other nostril closed.

Intranasal solutions are administered using a device manually actuated to deliver substance, and administration is confirmed by use of a breath monitoring device while holding the other nostril closed.

Intramuscular injections are performed into the brachial muscle using a disposable needle and syringe.

Intravenous injections are administered into the cephalic vein of the forearm using a disposable needle and syringe. Volume/amount administered per dose: 1.0 mL.

Sampling. Blood sampling for pharmacokinetic analyses is performed each dosing day. The sampling points are as follows: Before dosing, 2, 5, 10, 15, 20, 30, 45, 60, 120, 180, 240 and 480 minutes after dosing (total: 13 points). In certain instances a $14^{th}$ point at 25 minutes after dosing is also performed. Blood is drawn from the femoral vein with a syringe containing heparin sodium. The blood is immediately cooled on ice, centrifuged (4° C., 1710 cg, 3000 rpm, 15 minutes), and the plasma is stored in a deep freezer (−70° C. or below).

Pharmacokinetic Analysis. An LC/MS/MS analytical method is utilized for determination of DHE and 8'-hydroxy-DHE concentrations in plasma samples. $C_{max}$, $T_{max}$, $AUC_{0-t}$ and $T_{1/2}$ parameters are measured.

6.2.1 Results

Table 4 depicts the $C_{max}$, $T_{max}$, and AUC results from intranasal dosing of cynomolgous monkeys with 0.5 mg DHE mesylate nasal spray, that is, Migranal (liquid formulation) and the DHE powder formulations described in Example 1. The corresponding PK curves of DHE in monkey plasma after intranasal dosing with 0.5 mg of Migranal and 0.1, 0.5 and 1.0 mg of the intranasal DHE powder are shown in FIGS. 1 and 2. The data in Table 4 and FIGS. 1 and 2 show that the intranasal powder formulation maintains a short $T_{max}$ (17.5-30 min) over all doses tested. In this example, the $AUC_{0-t}$ (i.e., $AUC_{0-480}$ minutes) is tested 480 minutes after administration of the powder formulation or Migranal. Additionally, the pharmacokinetic profile of IN powder DHE is improved over the approved Migranal treatment. Specifically, the $T_{max}$ values resulting from the IN powder are shorter than that resulting from Migranal administration. Additionally, at the same DHE dose of 0.5 mg, the IN powder produces a 30% increase in DHE $C_{max}$ over Migranal. This improved PK is also reflected in FIG. 3, which shows that the DHE AUC in the first 30 minutes post-dosing is higher in monkeys when dosed with IN powder vs. Migranal.

TABLE 4

PK parameters of DHE in cynomolgous monkeys after intranasal dosing

| | $C_{max}$ (ng/ml) | $AUC_{0-t}$ (ng · h/mL) | $AUC_{0-inf}$ (ng · h/mL) | $T_{max}$ (min) |
|---|---|---|---|---|
| IN Powder (0.1 mg) | 1.82 | 5.01 | 5.72 | 17.5 |
| IN Powder (0.5 mg) | 6.00 | 18.76 | 22.25 | 30.0 |
| IN Powder (1.0 mg) | 7.59 | 27.90 | 33.96 | 29.0 |
| Migranal (0.5 mg) | 4.65 | 16.20 | 19.15 | 45.0 |

FIG. 4 shows a comparison of DHE pharmacokinetic plasma concentration curves when dosed with DHE intranasal powder (0.5 mg DHE) with and without caffeine. The results shown in FIG. 4 not only demonstrate that the $C_{max}$ was increased upon the addition of caffeine, but the $T_{max}$ was also lowered. Moreover, the results in FIG. 5 demonstrate that splitting the dose of DHE intranasal powder between two nostrils results in an increased DHE $C_{max}$ compared to administration of the full dose in one nostril.

6.2.2 Conclusions

The results of this example demonstrate that intranasal administration of powder formulations of dihydroergotamine described herein produce a rapid onset and good exposure to DHE in primate plasma. When compared with the FDA approved Migranal intranasal DHE formulation, the IN DHE powder formulations presented herein produce higher $C_{max}$ values and shorter $T_{max}$ values. Additionally, the exposure within the first 30 minutes post-administration is improved with the IN DHE powder formulations. The improvement in these PK parameters is particularly important in the treatment of migraine. Since DHE is generally administered to relieve an already occurring migraine, a faster onset and greater exposure to the drug in a short period of time is an optimal pharmacokinetic profile. Lastly, the plasma exposure to the drug is even further improved by adding caffeine to the IN DHE powder formulation and/or splitting the dose between two nostrils. These improvements in PK allow for administration of a lower dose of DHE to achieve therapeutically effective plasma levels.

6.3 Example 3

A Randomized, Open-Label, 5-Way Crossover Study to Evaluate the Pharmacokinetics, Dose Proportionality, Safety, and Tolerability of Single Doses of Dihydroergotamine 1, 1.5, 2 and 3 $m_2$ Intranasal Powder and Assess the Relative Bioavailability to Dihydroergotamine 1 mg Administered Subcutaneously as a Solution in Healthy Volunteers The study described herein is designed to determine the pharmacokinetic profile, dose-proportionality, safety and tolerability of DHE intranasal powder 1 mg, 1.5 mg, 2 mg and 3 mg in young healthy subjects and compare its bioavailability with DHE 1 mg administered subcutaneously as a solution. The pharmacokinetics of DHE and its metabolite (8'-β-hydroxydihydroergotamine; 8'-β-OH-DHE) are characterized in this study.

Methodology. This is a single-center, single-dose, randomized, open-label, 5-way crossover, pharmacokinetic and safety study. Thirty (30) eligible subjects, not less than 40% or more than 60% of either gender, receive study medication in each of 5 treatment periods. Subjects are randomly assigned to one of the 5 treatment sequences in accordance with a predetermined randomization schedule. The 5 treatment sequences are as follows in Table 5:

TABLE 5

| Sequence | Period 1 Treatment | Period 2 Treatment | Period 3 Treatment | Period 4 Treatment | Period 5 Treatment |
|---|---|---|---|---|---|
| 1 | A | E | B | C | D |
| 2 | B | A | C | D | E |
| 3 | C | B | D | E | A |
| 4 | D | C | E | A | B |
| 4 | E | D | A | B | C |

Treatment A = DHE 1 mg IN powder
Treatment B = DHE 1.5 mg IN powder
Treatment C = DHE 2 mg IN powder
Treatment D = DHE 3 mg IN powder
Treatment E = DHE 1 mg SC solution During each treatment period, subjects are confined for 36 hours approximately. Subjects are admitted in the early evening before dosing of the each treatment period (approximately 12 hours before drug administration) and remain in the clinical research unit until approximately 24 hours post-dose.

Study drug is administered in the morning, after an overnight fast of at least 10 hours. Multiple blood samples for PK analysis are drawn over 24 hours. A standardized lunch is provided within 4 to 5 hours after dosing. A standardized dinner is provided at approximately 1800 hours.

There is a washout period of not less than 7 days between treatment periods. The duration of the washout period is measured from the last day of the preceding period (approximately 24 hours post-dose) to dosing day of the subsequent period.

A safety follow-up visit takes place 7±2 days after the last treatment period.

Patient Inclusion Criteria. A subject is eligible for inclusion in this study only if all of the following criteria apply:

- Young healthy males or females, 18-45 years (inclusive) of age at the time of enrollment, who have provided signed Informed Consent and, if applicable, HIPAA authorization.
- Healthy as judged by a responsible physician with no clinically significant abnormality identified on the medical or laboratory evaluation, including 12-lead ECG. A subject with a clinical abnormality or laboratory parameters outside the reference range for this age group may be included only if the Investigator considers that the finding will not introduce additional risk factors and will not interfere with the study procedures.
- Subjects with a body mass index (BMI) >18 and <32 $kg/m^2$.
- Female subjects are included if they are post-menopausal or sterilized; or if they are of childbearing potential, they are not breastfeeding, have a negative pregnancy test, have no intention of becoming pregnant during the course of the study and are using adequate contraceptive drugs or devices during the course of this study. Medically acceptable methods of contraception that may be used by the subject and/or her partner are: oral contraceptives, progestin injection or implants, condom with spermicide, diaphragm with spermicide, IUD, vaginal spermicidal suppository combined with another barrier method of contraception (condom, diaphragm), hormonal patch and vaginal ring, surgical sterilization of their partner(s) or abstinence. Females using oral contraception must have started using the medication at least 4 weeks prior to screening. Surgical sterilization of partners must have occurred at least 6 weeks prior to screening.
- Non-smokers (refrained from any tobacco usage, including smokeless tobacco, nicotine patches, etc., for 6 months prior to the administration of the study medication).
- Subjects with intact nasal mucosa (no erythema, no inflammation, no ulceration, no swelling, no bleeding, no atrophy (severe local dryness and/or crusting), no septal perforation, and no other nasal conditions that may interfere with IN dosing.
- Subjects who are willing to abstain from alcohol for the 24 hours prior to first dose of study drug until the end of the blood sampling period after the last treatment period.
- Subjects who are willing and able to comply with the requirements of the protocol and follow directions from the clinic staff
- Subjects who are willing to avoid the consumption of grapefruit, pomelo and Seville orange products and juices within 24 hours prior to dosing of study drug until the end of the study.

Patient Exclusion Criteria. A subject is excluded from this study if any of the following criteria apply:

- Any clinically significant central nervous system (e.g., seizures), cardiac, pulmonary, metabolic, renal, hepatic or gastrointestinal conditions or history of such conditions that, in the opinion of the investigator may place the subject at an unacceptable risk as a participant in this trial or may interfere with the absorption, distribution, metabolism or excretion of drugs.
- Abnormal physical findings of clinical significance at the screening examination or baseline which would interfere with the objectives of the study.
- History of serious adverse reactions or hypersensitivity to any drug, or who are known to be allergic to any of the test product(s) or any components in the test product(s) or history of hypersensitivity or allergic reactions to any of the study preparations as described in the Investigator's Brochure.
- Clinically significant abnormal laboratory values (as determined by the Principal Investigator) at the screening evaluation.
- 12 lead ECG obtained at screening with: PR>240 msec, QRS>110 msec and QTc 430 msec, bradycardia (<50 bpm) or clinically significant minor ST wave changes on the screening ECG, or any other changes on the screening ECG that would interfere with measurement of the QT interval.
- History of orthostatic hypotension or orthostatic hypertension present at screening.
- Presence of an acute medical condition (e.g., diarrhea, fever, upper respiratory viral infection) within 14 days of first dosing in this study that is judged by the investigator to be clinically significant.
- Presence or history of allergies requiring acute or chronic treatment (except seasonal allergic rhinitis).
- Symptoms of a significant somatic or mental illness in the four week period preceding drug administration
- History or presence of migraine attacks in the last year.
- Surgical interventions within 6 months of the study.
- Has a positive pre-study Hepatitis B surface antigen; positive hepatitis C (HCV) antibody or detectable HCV ribonucleic acid (RNA); or positive HIV antibody result.
- History of sensitivity to 5-$HT_{1B/D}$ receptor agonists or to heparin (if the clinical research unit uses heparin to maintain intravenous cannula patency).
- Use of any prescription (e.g., ergotamine containing or ergot type medications (e.g., dihydroergotamine), or another 5-$HT_{1B/D}$ receptor agonists), or nonprescription medications, including vitamins and natural, herbal and dietary supplements within 7 days or 5 half-lives (whichever is longer) prior to the first dose of study medication, or use of St. John's Wort within 28 days prior to the first dose of study medication. However, the Investigator and study team can review medication use on a case by case basis to determine if its use would compromise subject safety or interfere with study procedures or data interpretation. By exception, the volunteer may take paracetamol or acetaminophen 2 g/day) or ibuprofen (1600 mg/day) up to 48 hours prior to the first dose of study medication. Subjects who use or have used other systemic prescription medications, or any drugs (or herbal preparations) known to inhibit CYP1A2 (for example fluvoxamine), CYP2D6 (for example paroxetine, quinidine and fluoxetine), or CYP3A (for example clarithromycin, itraconazole, ketoconazole, indinavir and erythromycin) or induce CYP1A2 (for example rifampin) or CYP3A (for example rifampin and carbamazepine) within 28 days prior to dosing.

History of drug abuse or dependence within 12 months of the study.

Has a history of regular alcohol consumption averaging >14 drinks/week (1 drink (12 g alcohol)=5 ounces (150 ml) of wine or 12 ounces (360 ml) of beer or 1.5 ounces (45 ml) of 80 proof distilled spirits) within 6 months of the screening visit.

Loss of 500 ml blood or more during the 3 month period before the study, e.g. blood donor.

The subject has a positive pre-study alcohol or urine drug screen. A minimum list of drugs that will be screened for include Amphetamines, Barbiturates, Cocaine, Opiates, Cannabinoids and Benzodiazepines. (Suspected false positive results may be repeated at the discretion of the Principal Investigator.)

Concurrent participation in another drug research study or within 60 days of enrollment.

Considered by the Investigator to be unsuitable candidate for this study.

Outcome Measures.

Pharmacokinetics. Pharmacokinetic sample collection: a total of 20 blood samples (6 mL each) are collected at the following times: 0 (pre-dose), 5, 10, 15, 20, 25, 30, 35, 40, and 45 minutes, and 1, 1.5, 2, 3, 4, 6, 8, 12, 18 and 24 hours post-dose.

Safety/Tolerability. The following assessment and measurements are conducted prior to dosing and/or at periodic intervals following dosing for up to 24 hours.

1. Physical examination
2. Vitals signs and body weight
3. 12-lead ECG
4. Blood tests for hematology and biochemistry analysis
5. Urinalysis
6. Adverse events (AEs)
7. Review of non-study medications received
8. Subjective assessment of nasal irritation: a questionnaire, answered by the subject, concerning the presence of various symptoms related to the nose
9. Brief Smell Identification Test (B-SIT™), a standardized test of olfactory function.
10. Objective assessment of nasal irritation: a structures examination of the nasal cavity and mucosal integrity.
11. Endoscopic examination of the nose if any clinical significant abnormalities were observed in any of the above 3 assessments.
12. Suicidal evaluation with the Columbia Suicide-Severity Rating Scale (C-SSRS).

Main Statistical Methods.

Pharmacokinetics. The following pharmacokinetic parameters are calculated for both DHE and its major metabolite, 8'-β-hydroxydihydroergotamine, using standard noncompartmental analysis:

1. Area under the concentration-time curves ($AUC_{0-\infty}$, and $AUC_{0-t}$)
2. Maximum observed plasma concentration ($C_{max}$)
3. Time to reach $C_{max}$ ($T_{max}$)
4. Terminal half-life ($t_{1/2}$)
5. Terminal rate constant (kel)
6. Ratio of $AUC_{0-t}$ to $AUC_{0-\infty}$ ($AUC_{0-t/0-\infty}$)

Statistical analyses are performed using SAS®. All PK parameters are calculated using the actual post-dose blood sampling times. Each time point is evaluated separately relative to the baseline value. Descriptive statistics [N, mean, standard deviation (SD), minimum, median, maximum and coefficient of variation (CV)] are used to summarize the PK parameters for each treatment.

The study endpoints are:

1. Pharmacokinetics and dose proportionality of DHE 1 mg, 1.5 mg, 2 mg and 3 mg intranasal powder. Dose proportionality will be determined by comparing $AUC_{0-\infty}$, $AUC_{0-t}$ and $C_{max}$ as estimated from plasma DHE and 8'-β-OH-DHE concentration profiles (Treatments A to D).
2. Pharmacokinetics of DHE 1 mg solution administered subcutaneously (Treatment E).
3. Relative bioavailability of the DHE 1 mg intranasal powder will be determined by comparing the $AUC_{0-t}$, $AUC_{0-\infty}$ and $C_{max}$ of the intranasal powder (Treatment A) to those of the DHE 1 mg subcutaneous solution (Treatment E).
4. Safety and tolerability of DHE in healthy adults following intranasal powder administration (Treatments A to D).
5. Examination and reporting of all safety measures (i.e. adverse events, vital signs and lab parameters) for all treatments in the study.

The relative bioavailability of the DHE intranasal powder vs. subcutaneous solution is determined by examining the 90% confidence interval for the ratios of the test group (Treatment A) mean 1n-transformed $AUC_{0-t}$, $AUC_{0-\infty}$ and $C_{max}$, relative to the reference group means (Treatment E).

Dose proportionality within Treatments A and D, is assessed by fitting the estimates of the 1n-transformed parameters $AUC_{0-\infty}$, $AUC_{0-t}$ and $C_{max}$ for both dose levels to the power model. Individual slopes are derived for each subject. The power model is fitted with log (dose) at fixed effect and subjects as a random effect. The estimated mean slope and 90% confidence intervals are constructed for each parameter. The primary criterion for dose proportionality for $AUC_{0-\infty}$, $AUC_{0-t}$ and $C_{max}$ is the inclusion of 1 within the range of the CIs, indicating the slope did not deviate significantly from 1.

Safety: Safety analyses are conducted for the safety population which is defined as any volunteer who received study medication.

Safety labs including CBC, chemistry and urinalysis findings are collected at baseline and end of each treatment period. Results from laboratory analyses are tabulated using descriptive statistics. A tabulation of by-volunteer abnormal/out-of-range findings is provided and changes from baseline to End of Period in all laboratory variables are tabulated.

A standard 12-lead ECG is obtained at screening, at the beginning and at the end of each treatment period and in the safety follow-up visit at the end of the study. A tabulation of by-volunteer abnormal/out-of-range findings is provided and changes from baseline to End of Study variables are tabulated.

6.4 Example 4

A Randomized, Open-Label, 5-Way Crossover Study to Evaluate the Pharmacokinetics, Bioavailability, Safety, and Tolerability of Single Doses of Dihydroergotamine 0.5 mg and 1 mg Intranasal Powder and Dihydroergotamine 0.5 mg Administered Intravenously, Intramuscularly and Intranasally as a Solution in Healthy Volunteers The study described herein is designed to determine the pharmacokinetic profile of DHE and its 8'-hydroxy-DHE metabolite, safety and tolerability of DHE intranasal powder 0.5 mg and 1 mg in young healthy subjects and compare its bioavailability with DHE 0.5 mg administered intravenously, intramuscularly or as an intranasal solution.

Methodology. This is a single-center, single-dose, randomized, open-label, 5-way crossover, pharmacokinetic and safety study. Thirty (30) eligible subjects, not less than 40% or more than 60% of either gender, receive study medication in each of 5 treatment periods. Subjects are randomly assigned to one of the 5 treatment sequences in accordance with a predetermined randomization schedule. The 5 treatment sequences are as follows in Table 6:

TABLE 6

| Sequence | Period 1 Treatment | Period 2 Treatment | Period 3 Treatment | Period 4 Treatment | Period 5 Treatment |
|---|---|---|---|---|---|
| 1 | A | E | B | C | D |
| 2 | B | A | C | D | E |
| 3 | C | B | D | E | A |
| 4 | D | C | E | A | B |
| 4 | E | D | A | B | C |

Treatment A = DHE 0.5 mg IN powder
Treatment B = DHE 1 mg IN powder
Treatment C = DHE 0.5 mg IN solution
Treatment D = DHE 0.5 mg IM solution
Treatment E = DHE 0.5 mg IV solution During each treatment period, subjects are confined for 36 hours approximately. Subjects are admitted in the early evening before dosing of the each treatment period (approximately 12 hours before drug administration) and remain in the clinical research unit until approximately 24 hours post-dose.

Study drug is administered in the morning, after an overnight fast of at least 10 hours. Multiple blood samples for PK analysis are drawn over 24 hours. A standardized lunch is provided within 4 to 5 hours after dosing. A standardized dinner is provided at approximately 1800 hours.

There is a washout period of not less than 7 days between treatment periods. The duration of the washout period is measured from the last day of the preceding period (approximately 24 hours post-dose) to dosing day of the subsequent period.

A safety follow-up visit takes place 7±2 days after the last treatment period.

Patient Inclusion Criteria. A subject is eligible for inclusion in this study only if all of the following criteria apply:

- Young healthy males or females, 18-45 years (inclusive) of age at the time of enrollment, who have provided signed Informed Consent and, if applicable, HIPAA authorization.
- Healthy as judged by a responsible physician with no clinically significant abnormality identified on the medical or laboratory evaluation, including 12-lead ECG. A subject with a clinical abnormality or laboratory parameters outside the reference range for this age group may be included only if the Investigator considers that the finding will not introduce additional risk factors and will not interfere with the study procedures.
- Subjects with a body mass index (BMI)≥18 and ≤32 $kg/m^2$.
- Female subjects are included if they are post-menopausal or sterilized; or if they are of childbearing potential, they are not breastfeeding, have a negative pregnancy test, have no intention of becoming pregnant during the course of the study and are using adequate contraceptive drugs or devices during the course of this study. Medically acceptable methods of contraception that may be used by the subject and/or her partner are: oral contraceptives, progestin injection or implants, condom with spermicide, diaphragm with spermicide, IUD, vaginal spermicidal suppository combined with another barrier method of contraception (condom, diaphragm), hormonal patch and vaginal ring, surgical sterilization of their partner(s) or abstinence. Females using oral contraception must have started using the medication at least 4 weeks prior to screening. Surgical sterilization of partners must have occurred at least 6 weeks prior to screening.
- Non-smokers (refrained from any tobacco usage, including smokeless tobacco, nicotine patches, etc., for 6 months prior to the administration of the study medication).
- Subjects with intact nasal mucosa (no erythema, no inflammation, no ulceration, no swelling, no bleeding, no atrophy (severe local dryness and/or crusting), no septal perforation, and no other nasal conditions that may interfere with IN dosing.
- Subjects who are willing to abstain from alcohol for the 24 hours prior to first dose of study drug until the end of the blood sampling period after the last treatment period.
- Subjects who are willing and able to comply with the requirements of the protocol and follow directions from the clinic staff
- Subjects who are willing to avoid the consumption of grapefruit, pomelo and Seville orange products and juices within 24 hours prior to dosing of study drug until the end of the study.

Patient Exclusion Criteria. A subject is ineligible for inclusion in this study if any of the following criteria apply:

- Any clinically significant central nervous system (e.g., seizures), cardiac, pulmonary, metabolic, renal, hepatic or gastrointestinal conditions or history of such conditions that, in the opinion of the investigator may place the subject at an unacceptable risk as a participant in this trial or may interfere with the absorption, distribution, metabolism or excretion of drugs.
- Abnormal physical findings of clinical significance at the screening examination or baseline which would interfere with the objectives of the study.
- History of serious adverse reactions or hypersensitivity to any drug, or who are known to be allergic to any of the test product(s) or any components in the test product(s) or history of hypersensitivity or allergic reactions to any of the study preparations as described in the Investigator's Brochure.
- Clinically significant abnormal laboratory values (as determined by the Principal Investigator) at the screening evaluation.
- 12 lead ECG obtained at screening with: PR>240 msec, QRS>110 msec and QTc 430 msec, bradycardia (<50 bpm) or clinically significant minor ST wave changes on the screening ECG, or any other changes on the screening ECG that would interfere with measurement of the QT interval.
- History of orthostatic hypotension or orthostatic hypertension present at screening.
- Presence of an acute medical condition (e.g., diarrhea, fever, upper respiratory viral infection) within 14 days of first dosing in this study that is judged by the investigator to be clinically significant.
- Presence or history of allergies requiring acute or chronic treatment (except seasonal allergic rhinitis).

Symptoms of a significant somatic or mental illness in the four week period preceding drug administration History or presence of migraine attacks in the last year.

Surgical interventions within 6 months of the study.

Has a positive pre-study Hepatitis B surface antigen; positive hepatitis C (HCV) antibody or detectable HCV ribonucleic acid (RNA); or positive HIV antibody result.

History of sensitivity to 5-$HT_{1B/D}$ receptor agonists or to heparin (if the clinical research unit uses heparin to maintain intravenous cannula patency).

Use of any prescription (e.g., ergotamine containing or ergot type medications (e.g., dihydroergotamine), or another 5-$HT_{1B/D}$ receptor agonists), or nonprescription medications, including vitamins and natural, herbal and dietary supplements within 7 days or 5 half-lives (whichever is longer) prior to the first dose of study medication, or use of St. John's Wort within 28 days prior to the first dose of study medication. However, the Investigator and study team can review medication use on a case by case basis to determine if its use would compromise subject safety or interfere with study procedures or data interpretation. By exception, the volunteer may take paracetamol or acetaminophen (≥2 g/day) or ibuprofen (1600 mg/day) up to 48 hours prior to the first dose of study medication.

Subjects who use or have used other systemic prescription medications, or any drugs (or herbal preparations) known to inhibit CYP1A2 (for example fluvoxamine), CYP2D6 (for example paroxetine, quinidine and fluoxetine), or CYP3A (for example clarithromycin, itraconazole, ketoconazole, indinavir and erythromycin) or induce CYP1A2 (for example rifampin) or CYP3A (for example rifampin and carbamazepine) within 28 days prior to dosing.

History of drug abuse or dependence within 12 months of the study.

Has a history of regular alcohol consumption averaging >14 drinks/week (1 drink (12 g alcohol)=5 ounces (150 ml) of wine or 12 ounces (360 ml) of beer or 1.5 ounces (45 ml) of 80 proof distilled spirits) within 6 months of the screening visit.

Loss of 500 ml blood or more during the 3 month period before the study, e.g. blood donor.

The subject has a positive pre-study alcohol or urine drug screen. A minimum list of drugs that will be screened for include Amphetamines, Barbiturates, Cocaine, Opiates, Cannabinoids and Benzodiazepines. (Suspected false positive results may be repeated at the discretion of the Principal Investigator.)

Concurrent participation in another drug research study or within 60 days of enrollment.

Considered by the Investigator to be unsuitable candidate for this study.

Outcome Measures.

Pharmacokinetics: Pharmacokinetic sample collection: a total of 20 blood samples (6 mL each) are collected at the following times: 0 (pre-dose and immediately post-dose in the IV arm), 5, 10, 15, 20, 25, 30, 35, 40, and 45 minutes, and 1, 1.5, 2, 3, 4, 6, 8, 12, 18 and 24 hours post-dose.

Safety/Tolerability: The following assessment and measurements will be conducted prior to dosing and/or at periodic intervals following dosing for up to 24 hours.

Physical examination

Vitals signs and body weight 12-lead ECG

Blood tests for hematology and biochemistry analysis

Urinalysis

Adverse events (AEs)

Review of non-study medications received

Subjective assessment of nasal irritation: a questionnaire, answered by the subject, concerning the presence of various symptoms related to the nose Brief Smell Identification Test (B-SIT™), a standardized test of olfactory function.

Objective assessment of nasal irritation: a structures examination of the nasal cavity and mucosal integrity.

Endoscopic examination of the nose if any clinical significant abnormalities were observed in any of the above 3 assessments.

Suicidal evaluation with the Columbia Suicide-Severity Rating Scale (C-SSRS).

Main Statistical methods (including required subject number requirement):

Pharmacokinetics. The following pharmacokinetic parameters are calculated for both DHE and its major metabolite, 8-β-hydroxydihydroergotamine, using standard noncompartmental analysis:

1. Area under the concentration-time curves ($AUC_{0\infty}$, and $AUC_{0-t}$)
2. Maximum observed plasma concentration ($C_{max}$)
3. Time to reach $C_{max}$ ($T_{max}$)
4. Terminal half-life ($t_{1/2}$)
5. Terminal rate constant (kel)
6. Ratio of $AUC_{0-t}$ to $AUC_{0-\infty}$ ($AUC_{0-t}/_{0-\infty}$)

Statistical analyses are performed using SAS®. Plasma concentrations and pharmacokinetic parameters are summarized descriptively by treatment group and time point, where appropriate. All PK parameters are calculated using the actual post-dose blood sampling times. Each time point is evaluated separately relative to the baseline value. Descriptive statistics [N, mean, standard deviation (SD), minimum, median, maximum and coefficient of variation (CV)] are used to summarize the PK parameters for each treatment.

The study endpoints are:

1. Pharmacokinetics and dose proportionality of DHE 0.5 and 1 mg intranasal powder. Dose proportionality is determined by comparing $AUC_{0-\infty}$, $AUC_{0-t}$ and $C_{max}$ as estimated from plasma DHE and 8'-β-OH-DHE concentration profiles (Treatments A and B).
2. Pharmacokinetics of DHE 0.5 mg solution administered intravenously, intramuscularly and intranasally (Treatments C, D and E).
3. Absolute and relative bioavailability of the DHE 0.5 mg intranasal powder are determined by comparing the $AUC_{0-t}$, $AUC_{0-\infty}$ and $C_{max}$ of the intranasal powder (Treatment A) to those of the DHE 0.5 mg intravenous, intramuscular and intranasal solutions (Treatments C, D and E).
4. Safety and tolerability of DHE in healthy adults following intranasal powder administration (Treatments A and B).
5. Examination and reporting of all safety measures (i.e. adverse events, vital signs and lab parameters) for all treatments in the study.

The absolute and relative bioavailability of the DHE intranasal powder vs. intravenous and intramuscular and intranasal solution are determined by examining the 90% confidence interval for the ratios of the test group (Treatment A) mean 1n-transformed $AUC_{0-t}$, $AUC_{0-\infty}$ and $C_{max}$, relative to the reference group means (Treatments C, D, and E).

Dose proportionality within Treatments A and B, are assessed by fitting the estimates of the 1n-transformed parameters $AUC_{0-\infty}$, $AUC_{0-t}$ and $C_{max}$ for both dose levels to the power model. Individual slopes will be derived for each subject. The power model is fitted with log (dose) at fixed effect and subjects as a random effect. The estimated mean slope and 90% confidence intervals are constructed for each parameter. The primary criterion for dose proportionality for $AUC_{0-\infty}$, $AUC_{0-t}$ and $C_{max}$ is the inclusion of 1 within the range of the CIs, indicating the slope did not deviate significantly from 1.

Safety. Safety analyses are conducted for the safety population which is defined as any volunteer who received study medication.

All adverse events reported during the study are listed, documenting course, severity, possible relationship to study medication and outcome. Verbatim terms on the case report forms are classified to preferred terms and related system organ class using the MedDRA dictionary. The preferred terms and system organ classes are tabulated by treatment group and study period. All reported adverse events are summarized by the number of volunteers reporting adverse events, system organ class, preferred term, severity and relationship to study drug. All adverse events are presented in data listings indexed by volunteer.

Safety labs including CBC, chemistry and urinalysis findings are collected at baseline and end of each treatment period. Results from laboratory analyses are tabulated using descriptive statistics. A tabulation of by-volunteer abnormal/out-of-range findings is provided and changes from baseline to End of Period in all laboratory variables are tabulated.

A standard 12-lead ECG is obtained at screening, at the beginning and at the end of each treatment period and in the safety follow-up visit at the end of the study. A tabulation of by-volunteer abnormal/out-of-range findings is provided and changes from baseline to End of Study variables are tabulated.

6.5 Example 5

Treatment of Migraine with Dihydroergotamine Intranasal Powder Formulation

The DHE nasal powder formulation is indicated for rapid onset treatment of acute migraine with or without aura. Patients are instructed to use the product when they have an active migraine headache. Specifically, prior to use, patients are instructed to blow their nose gently to help open the nasal passages. If the entire dose is to be delivered in a single nostril, the patient is instructed to select the nostril with the better airflow. Some physicians may consider using the DHE nasal powder in their office or in a medical setting. The total amount of DHE in a single dose ranges from about 0.1 to 10 mg. Typically, a patient receives a dose of about 1.0 to 2.0 mg. DHE nasal powder with or without caffeine may be administered to the patient.

DHE Nasal Powder Presentation. The DHE nasal powder formulation is delivered using a dispenser. The dispenser primarily consists of a squeeze bottle with a nozzle approximately half an inch long. The squeeze bottle functions as a pump and the nozzle, which normally holds the powder at its base, also targets and guides the delivery of the powder into the nostril. The squeeze bottle can be configured as a disposable single-unit dose delivery system or a multiple dose delivery. It can also be configured to be refilled with the powder once the pre-filled dispenser is fully used. The dispenser containing the formulation can also be configured to deliver each dose in a single or a double puff without priming. The powder from the dispenser can be administered in either nostril or both nostrils.

Exclusions. Patients are instructed not to use the product to prevent a headache if they have no prodromal symptoms of migraine such as changes in mental state including irritability or confusion, and physical signs including thirst or diarrhea. Any migraine patient who is pregnant or nursing, has any cardiovascular diseases, or taking anti-HIV medications, or taking macrolide antibiotic such as troleandomycin, clarithromycin or erythromycin is instructed not to use the DHE nasal powder formulation. Similarly, migraine patients taking triptans are instructed not to use the DHE nasal powder and conversely, patients using the DHE nasal powder are instructed not to simultaneously use triptans for the treatment of migraine.

INCORPORATION BY REFERENCE

Various references such as patents, patent applications, and publications are cited herein, the disclosures of which are hereby incorporated by reference herein in their entireties. In the event of a conflict between a term herein and a term incorporated by reference, the term herein controls.

What is claimed is:

1. A nasal delivery device, comprising a pharmaceutical nasal dosage form comprising dihydroergotamine mesylate and microcrystalline cellulose;

wherein dihydroergotamine mesylate is present in the pharmaceutical nasal dosage form in an amount of 6 mg to about 8 mg, wherein said microcrystalline cellulose is present in the pharmaceutical nasal dosage form in an amount from about 40% to about 60% w/w; and wherein said pharmaceutical nasal delivery device provides a $T_{max}$ of dihydroergotamine mesylate of less than or equal to about 30 minutes; and the nasal delivery device requires no priming.

2. The nasal delivery device of claim 1, wherein said dihydroergotamine mesylate is present in about 18% w/w of said pharmaceutical nasal dosage form.

3. The nasal delivery device of claim 1, wherein said dihydroergotamine mesylate is present in about 23% w/w of said pharmaceutical nasal dosage form.

4. The nasal delivery device of claim 1, wherein said dihydroergotamine mesylate is present in an amount of 6 mg.

5. The nasal delivery device of claim 1, wherein the pharmaceutical nasal dosage form is a powder pharmaceutical nasal dosage form.

6. The nasal delivery device of claim 1, wherein the pharmaceutical nasal dosage form is in a unit dose form.

7. The nasal delivery device of claim 1, wherein the microcrystalline cellulose is present in an amount of about 50% to about 60% of the total weight of said pharmaceutical nasal dosage form.

8. The nasal delivery device of claim 7, wherein the microcrystalline cellulose is present in an amount of about 60% of a total weight of said pharmaceutical nasal dosage form.

9. The nasal delivery device of claim 1, wherein said microcrystalline cellulose has a mean particle size diameter of about 100 μm or less.

10. The nasal delivery device of claim 9, wherein said microcrystalline cellulose has a mean particle size diameter of about 50 μm or less.

11. The nasal delivery device of claim 10, wherein said microcrystalline cellulose has a mean particle size diameter of about 30 μm or less.

12. The nasal delivery device of claim 5, wherein the total weight of the powder pharmaceutical nasal dosage form is about 35 mg.

13. The nasal delivery device of claim 12 wherein the total weight of the powder pharmaceutical nasal dosage form is about 30 mg.

14. A method of delivering the nasal pharmaceutical dosage form, comprising:

administering to a nostril of a subject the pharmaceutical nasal dosage form by the nasal delivery device of claim 1.

15. A method of treating a headache, comprising:

administering to a nostril of a subject the pharmaceutical nasal dosage form by the nasal delivery device of claim 1.

16. The method of claim 14, wherein the pharmaceutical nasal dosage form is administered at a first time and a second time.

* * * * *